US010092564B2

(12) United States Patent
Moussy et al.

(10) Patent No.: US 10,092,564 B2
(45) Date of Patent: Oct. 9, 2018

(54) USE OF MASITINIB FOR TREATMENT OF AN AMYOTROPHIC LATERAL SCLEROSIS PATIENT SUBPOPULATION

(71) Applicant: AB SCIENCE, Paris (FR)

(72) Inventors: Alain Moussy, Paris (FR); Jean-Pierre Kinet, Lexington, MA (US); Colin Mansfield, Ecully (FR)

(73) Assignee: AB SCIENCE, Paris (FR)

( * ) Notice: Subject to any disclaimer, the term of this patent is extended or adjusted under 35 U.S.C. 154(b) by 0 days.

(21) Appl. No.: 15/545,800

(22) PCT Filed: Mar. 24, 2017

(86) PCT No.: PCT/EP2017/057134
§ 371 (c)(1),
(2) Date: Jul. 24, 2017

(87) PCT Pub. No.: WO2017/162884
PCT Pub. Date: Sep. 28, 2017

(65) Prior Publication Data
US 2018/0117037 A1 May 3, 2018

(30) Foreign Application Priority Data
Mar. 25, 2016 (EP) .................... 16162490

(51) Int. Cl.
A61K 31/496 (2006.01)
A61K 31/428 (2006.01)
A61K 9/00 (2006.01)
A61P 25/00 (2006.01)

(52) U.S. Cl.
CPC .......... A61K 31/496 (2013.01); A61K 9/0053 (2013.01); A61K 31/428 (2013.01); A61P 25/00 (2018.01)

(58) Field of Classification Search
CPC ... A61K 31/496; A61K 31/428; A61K 9/0053
USPC ..................................................... 514/253.1
See application file for complete search history.

(56) References Cited

U.S. PATENT DOCUMENTS 7,423,055 B2   9/2008  Ciufolini et al.
2011/0201620 A1  8/2011  Ciufolini et al.

FOREIGN PATENT DOCUMENTS

| CA | 2093203 C | 10/1993 |
| EP | 0564409 A1 | 10/1993 |
| EP | 1525200 B1 | 10/2007 |
| WO | 99/03854 A1 | 1/1999 |
| WO | 2008/098949 A2 | 8/2008 |
| WO | 2011/131705 A1 | 10/2011 |
| WO | 2013/010015 A2 | 1/2013 |
| WO | 2014/145909 A2 | 9/2014 |
| WO | 2015/063318 A1 | 5/2015 |

OTHER PUBLICATIONS

Wijesekera, et al., "Amyotrophic Lateral Sclerosis," Orphanet J Rare Dis., 2009, vol. 4, No. 3, pp. 1-22.
Philips, et al., "Neuroinflammation in Amyotrophic Lateral Sclerosis: Role of Glial Activation in Motor Neuron Disease," Lancet Neurol., 2011, vol. 10, pp. 253-263.
Turner, et al., "Evidence of Widespread Cerebral Microglial Activation in Amyotrophic Lateral Sclerosis: An [11C](R)-PK11195 Positron Emission Tomography Study," Neurobiology of Disease, 2004, vol. 15, No. 3, pp. 601-609.
Garbuzova-Davis, et al., "Implications of Blood-Brain Barrier Disruption in ALS," Amyotrophic Lateral Sclerosis, 2008, vol. 9, No. 6, pp. 375-376.
Skaper, et al., "Mast cells, Glia and Neuroinflammation: Partners in Crime?," Immunology, 2014, vol. 141, No. 3, pp. 314-327.
Kimura, et aL, "Progression Rate of ALSFRS-R at Time of Diagnosis Predicts Survival Time in ALS," Neurology, 2006, vol. 66, No. 2, pp. 265-267.
Miller, et al., "Riluzole for Amyotrophic Lateral Sclerosis (ALS)/Motor Neuron Disease (MND)," Cochrane Database Syst Rev., 2012, Issue 3, pp. 1-36.
Jenkins, et al., "The Evidence for Symptomatic Treatments in Amyotrophic Lateral Sclerosis," Current Opinion Neurology, 2014, vol. 27, No. 5, pp. 524-531.
Ashworth, et al., "Treatment for Spasticity in Amyotrophic Lateral Sclerosis/Motor Neuron Disease, Cochrane Database Syst Rev., 2006, vol. 1, pp. 1-16.
Cedarbaum, et al, "The ALSFRS-R: A Revised ALS Functional Rating Scale that Incorporates Assessments of Respiratory Function," Journal Neurological Sciences, 1999, vol. 169, pp. 13-21.
Berry, et al., "The Combined Assessment of Function and Survival (CAFS): A New Endpoint for ALS Clinical Trials," Amyotrophic Lateral Sclerosis and Frontotemporal Degeneration, 2013, vol. 14, No. 3, pp. 162-168.
Traynor, et al., "Functional Outcome Measures as Clinical Trial Endpoints in ALS," Neurology, 2004, vol. 63, vol. 10, pp. 1933-1935.
Dubreuil et al., "Masitinib (AB1010), A Potent and Selective Tyrosine Kinase Inhibitor Targeting KIT," PLoS ONE, 2009, vol. 4, No. 9, pp. 1-12.
Davis et al., "Comprehensive Analysis of Kinase Inhibitor Selectivity," Nature Biotechnology, 2011, vol. 29, No. 11, pp. 1046-1051.
Nautiyal, et al., "Brain Mast Cells Link the Immune System to Anxiety-Like Behavior," PNAS, 2008, vol. 105, No. 46, pp. 18053-18057.
Theoharides, et al., "Critical Role of Mast Cells in Inflammatory Diseases and the Effect of Acute Stress," Journal of Neuroimmunology, 2004, vol. 146, pp. 1-12.
Silverman, et al., "Mast Cells Migrate from Blood to Brain," Journal of Neuroscience, 2000, vol. 20, No. 1, pp. 401-408.

(Continued)

Primary Examiner — Yevgeny Valenrod
(74) Attorney, Agent, or Firm — Young & Thompson

(57) ABSTRACT

Disclosed is a method for treating patients afflicted with non-aggressive or moderately aggressive amyotrophic lateral sclerosis (ALS) whose rate of change of the revised Amyotrophic Lateral Sclerosis Functional Rating Scale (ALSFRS-R) prior to treatment initiation is <1.1 points per month, the method including administering a tyrosine kinase inhibitor or mast cell inhibitor, in particular masitinib, or a pharmaceutically acceptable salt or solvate thereof, optionally in combination with at least one pharmaceutically active ingredient.

20 Claims, No Drawings

(56) References Cited

OTHER PUBLICATIONS

Guan, et al., "Injured Sensory Neuron-Derived CSF1 Induces Microglia Proliferation and DAP12-Dependent Pain," Nat Neurosci., 2016; vol. 19, No. 1, pp. 94-101.
Brooks, "El Escorial World Federation of Neurology Criteria for the Diagnosis of Amyotrophic Lateral Sclerosis," Journal of the Neurological Sciences, 1994, vol. 124, pp. 96-107.
International Search Report issued in Application No. PCT/EP2017/057134, dated May 17, 2017.
Katsumata, et al., "c-Abl inhibition Delays Motor Neuron Degeneration in the G93A Mouse, An Animal Model of Amyotrophic Lateral Sclerosis," PLoS One, 2012, vol. 7, No. 9, pp. 1-14.
"A Prospective, Multicenter, Randomized, Double-Blind, Placebocontrolled, Parallel Group, Phase 2 Study to Compare the Efficiency and Safety of Masitinib Versus Placebo in the Treatment of Patients Suffering from Amyotrophic Lateral Sclerosis (ALS)," EU Clinical Trials Register, 2012, 9 pages.
Trieu et al., "A Specific Inhibitor of Janus Kinase-3 Increases Survival in a Transgenic Mouse Model of Amyotrophic Lateral Sclerosis," Biochemical and Biophysical Research Communications, 2000, vol. 267, pp. 22-25.
Miller, "Riluzole for ALS: What is the Evidence?," Amyotrophic Lateral Sclerosis Other Motor Neuron Disorders, 2003; vol. 4, No. 3, 2 pages.

USE OF MASITINIB FOR TREATMENT OF AN AMYOTROPHIC LATERAL SCLEROSIS PATIENT SUBPOPULATION

FIELD OF INVENTION

The present invention relates to a method for treating patients afflicted with non-aggressive or moderately aggressive amyotrophic lateral sclerosis (ALS) whose rate of change of the revised Amyotrophic Lateral Sclerosis Functional Rating Scale (ALSFRS-R) prior to treatment initiation is <1.1 points per month said method comprising administering a tyrosine kinase inhibitor or mast cell inhibitor, in particular masitinib or a pharmaceutically acceptable salt or solvate thereof, optionally in combination with at least one pharmaceutically active ingredient.

BACKGROUND OF INVENTION

Amyotrophic lateral sclerosis (ALS) is a neurodegenerative disease characterized by progressive muscular paralysis reflecting degeneration of motor neurons in the primary motor cortex, corticospinal tracts, brainstem and spinal cord [Wijesekera L C, et al. Orphanet J Rare Dis. 2009 Feb. 3; 4:3].

Approximately two thirds of patients with typical ALS have a spinal form of the disease (limb onset) and present with symptoms related to focal muscle weakness and wasting, in which onset of symptoms may start either distally or proximally in the upper and lower limbs. Gradually, spasticity may develop in the weakened atrophic limbs, affecting manual dexterity and gait. Patients with bulbar onset ALS usually present with dysarthria and dysphagia for solids or liquids. Limb symptoms can develop almost simultaneously with bulbar symptoms and in the vast majority of cases will occur within 1-2 years. Paralysis is progressive and leads to death due to respiratory failure within 2-3 years for bulbar onset cases and 3-5 years for limb onset ALS cases.

Most ALS cases are sporadic but 5-10% of cases are familial, and of these 20% involve a mutation of the SOD1 gene (21q22.11), about 2-5% involve mutations of the TARDBP gene (1p36.22) encoding the TAR DNA-binding protein 43 (TDP-43) and 1-2% involve mutations of the VCP gene (9p13.3) coding for the Valosin Containing Protein. Two percent of apparently sporadic cases involve SOD1 mutations, and TARDBP mutations have also been identified in sporadic cases.

The cause of ALS is unknown although some genetic risk factors have been identified. Recent reviews on the role of environmental risk factors in the causation of ALS have concluded that there is no consistent association between a single environmental factor and risk of developing ALS. Most authors favor a hypothesis of complex genetic-environmental interaction as the causal factor for motor neuron degeneration.

The exact molecular pathway causing motor neuron degeneration in ALS is unknown, but as with other neurodegenerative diseases it is likely to involve a complex interplay between multiple pathogenic cellular mechanisms, which may not be mutually exclusive. These include: genetic factors, excitotoxicity, oxidative stress, mitochondrial dysfunction, impaired axonal transport, neurofilament aggregation, protein aggregation, inflammatory dysfunction and contribution of non-neuronal cells.

There is growing evidence that inflammatory dysfunction and non-neuronal cells may play a part in pathogenesis of ALS [Wijesekera L C, et al. Orphanet J Rare Dis. 2009 Feb. 3; 4:3]. Microglial and dendritic cell activation is a prominent pathology in human ALS and transgenic SOD1 mice. These activated non-neuronal cells produce inflammatory cytokines such as interleukins, COX-2, TNFα and MCP-1, and evidence of upregulation is found in cerebrospinal fluid or spinal cord specimens of ALS patients or in vitro models. Neuroinflammation via glial activation is now established as an important aspect of pathology in ALS [Philips T, et al. Lancet Neurol. 2011; 10: 253-263]. There is a marked activation or proliferation of both microglia and astrocytes at specific disease stages in humans in vivo [Turner M R, et al. Neurobiol Dis 2004; 15:601-9]. There is also evidence indicating impairment of all neurovascular unit components including the blood-brain and blood-spinal cord barriers in both patients and animal models of ALS [Garbuzova-Davis S. Amyotroph Lateral Scler. 2008 December; 9(6):375-6].

Another non-neuronal cell of emerging significance is the mast cell. Mast cells are well known to play a prominent role in all inflammatory processes through expressing receptors for molecules that are usually involved in such reactions. Furthermore, mast cells release large amounts of various mediators that sustain the inflammatory network and modulate blood-brain barrier (BBB) permeability [Skaper S D, et al. Immunol 2014; 141:314-327]. Importantly, mast cells and neuronal cells are linked through the activation of microglia in response to pro-inflammatory cytokines released from mast cells [Skaper S D, et al. Immunol 2014; 141:314-327].

It has been observed in clinical practice that ALS patients experience different rates of disease progression. It is hypothesized that different rates of disease progression reflect differing pathogenesis of ALS, with ramifications as to the efficacy of therapies directed towards any specific mechanism of disease. That is to say, heterogeneity within the overall ALS population in terms of disease progression can be explained by distinct subpopulations of ALS patients.

There exist at least two highly distinct subpopulations of ALS patient within the overall ALS population, which can be distinguished from one another in terms of 'fast progressor' patients (referred to also as 'aggressive ALS') who progress at a relatively fast rate as measured via progression of a suitable clinical marker of disease burden, and 'normal progressor' patients (referred to also as 'non-aggressive or moderately aggressive ALS') who progress at a relatively slower rate. The former subgroup represents a more aggressive and heterogeneous form of disease with patients at higher risk of death (significantly shorter median survival time) or tracheostomy [Kimura F, et al. Neurology 2006; 66:265-267]. The latter "normal progressor" subgroup represents the majority of ALS patients.

There is no available treatment to stop or reverse the progressive course of ALS, whether is it non-aggressive or moderately aggressive ALS or aggressive ALS. There has been no advance in efficacy of available therapeutic agents over the last 20 years since registration of riluzole, the only authorized medicinal product for ALS. This is despite the fact that riluzole (100 mg) offers only modest survival benefits, very modest functional improvement and is an expensive drug, estimated to cost approximately $10,000 per year per patient in the US.

A comprehensive review by Miller and colleagues on the use of riluzole for ALS considered evidence from four randomized clinical trials involving 1477 ALS patients treated with riluzole [Miller R G, et al. Cochrane Database Syst Rev. 2012 Mar. 14; 3:CD001447]. Results from this meta-analysis indicated that riluzole 100 mg probably prolongs median survival in people with ALS by 2 to 3 months with respect to participants taking placebo and the safety of the drug is not a major concern. There are no data that directly measured quality of life from the published trials. Additionally, there was no beneficial effect of riluzole on patient function in any of the randomized trials considered separately. Only when data were combined was small beneficial effect on bulbar and limb function observed, but not on muscle strength; the authors however, warn that these functional results should be interpreted with caution.

Many symptomatic treatments, which do not slow disease progression but affect quality of life, appear helpful to individuals in the clinical setting (Table 1 lists the various symptomatic treatments commonly used for management of ALS [Jenkins T M, et al. Curr Opin Neurol. 2014 October; 27(5):524-31]). However, evidence of significant benefit is weak and further randomized clinical trials are required to provide a more robust evidence base. This opinion is reflected in a Cochrane systematic review of treatments for spasticity in ALS by Ashworth and colleagues (published in 2006 with update in 2011) [Ashworth N L, et al. Cochrane Database of Systematic Reviews 2006, Issue 1. Art. No.: CD004156].

TABLE 1

Summary of symptomatic treatments commonly used in patients with ALS [adapted from Jenkins 2014]

| Drug | Population indicated/Common usage |
|---|---|
| Baclofen (Lioresal) | Indicated for the relief of spasticity of voluntary muscle resulting from such disorders, for example, multiple sclerosis. In patients 0 to <18 years it is indicated for the symptomatic treatment of spasticity of cerebral origin, including ALS. |
| Hyoscine | Hypersalivation |
| Carbocisteine | Difficulty expectorating secretions |
| Amitriptyline | Neuropathic pain |
| Gabapentin | Neuropathic pain |
| Citalopram | Depression and emotional lability |
| Venlafaxine | Depression |
| Nortriptyline | Depression |

In conclusion, the treatment of ALS remains a challenge to clinicians because of the diversity and complexity of the disease itself and the lack of standard and clinically meaningful effective therapy.

Furthermore, existing treatments do not take into account the progression rate of the disease, i.e. non-aggressive or moderately aggressive ALS versus aggressive ALS.

None of the known approved or investigational drugs appear to represent a cure for ALS. Moreover, the efficacy of known drugs is limited and may decrease over time, with undesirable side effects reported. Thus, there exists a continuing need to identify new targeted drugs that possess greater efficacy to treat ALS, and in particular the non-aggressive or moderately aggressive ALS affecting the majority of ALS patients.

SUMMARY

The present invention thus relates to a method for treating non-aggressive or moderately aggressive amyotrophic lateral sclerosis (ALS) comprising administering a tyrosine kinase inhibitor or a pharmaceutically acceptable salt or solvate thereof, optionally in combination with at least one pharmaceutically active ingredient, to a subject in need thereof.

The present invention also relates to a method for treating non-aggressive or moderately aggressive ALS comprising administering an inhibitor of at least one tyrosine kinase selected from c-Kit, Lyn, Fyn, PDGFR, and CSF1R, or any combination thereof, optionally in combination with at least one pharmaceutically active ingredient, to a subject in need thereof.

The invention aims to solve the technical problem of providing an active ingredient for the treatment of patients afflicted with non-aggressive or moderately aggressive ALS.

In one embodiment, non-aggressive or moderately aggressive ALS is defined as a progression of the revised Amyotrophic Lateral Sclerosis Functional Rating Scale (ALSFRS-R) score before treatment initiation of less than 1.1 points per month.

In another embodiment, non-aggressive or moderately aggressive ALS is defined as a rate of change of ALSFRS-R score from the date of first ALS-related symptom to time of first treatment (baseline) of less than 1.1 points per month.

In one embodiment, non-aggressive ALS is defined as a progression of the revised Amyotrophic Lateral Sclerosis Functional Rating Scale (ALSFRS-R) score before treatment initiation of less than 0.8 points per month. In another embodiment, non-aggressive ALS is defined as a rate of change of ALSFRS-R score from the date of first ALS-related symptom to time of first treatment (baseline) of less than 0.8 points per month.

In one embodiment, moderately aggressive ALS is defined as a progression of the revised Amyotrophic Lateral Sclerosis Functional Rating Scale (ALSFRS-R) score before treatment initiation of less than 1.1 points per month and equal to or greater than 0.8 points per month (≥0.8 to <1.1 points per month). In another embodiment, moderately aggressive ALS is defined as a rate of change of ALSFRS-R score from the date of first ALS-related symptom to time of first treatment (baseline) of less than 1.1 points per month and equal to or greater than 0.8 points per month (≥0.8 to <1.1 points per month).

This invention thus also relates to a method for treating patients with non-aggressive or moderately aggressive ALS (i.e. patient whose progression of ALSFRS-R score before treatment initiation is less than 1.1 points per month), comprising administering a tyrosine kinase inhibitor or a pharmaceutically acceptable salt or solvate thereof, preferably masitinib or a pharmaceutically acceptable salt or solvate thereof, optionally in combination with at least one pharmaceutically active ingredient, to subject in need thereof.

The invention relates to a method for treating patients suffering from amyotrophic lateral sclerosis (ALS) having a progression of ALSFRS-R score before treatment initiation of less than 1.1 points per month, comprising administering a tyrosine kinase inhibitor or a pharmaceutically acceptable salt or solvate thereof, preferably masitinib or a pharmaceutically acceptable salt or solvate thereof, optionally in combination with at least one pharmaceutically active ingredient, to subject in need thereof.

In one embodiment, patients have a progression of ALSFRS-R score before treatment initiation of less than 0.8 points per month. In another embodiment, patients have a progression of ALSFRS-R score before treatment initiation of less than 1.1 points per month and equal to or greater than 0.8 points per month (≥0.8 to <1.1 points per month).

This invention further relates to an inhibitor of at least one tyrosine kinase selected from c-Kit, Lyn, Fyn, PDGFR and CSF1R, or any combination thereof, preferably masitinib or a pharmaceutically acceptable salt or solvate thereof, for use for treating patients with non-aggressive or moderately aggressive ALS (i.e. patient whose progression of ALS-FRS-R score before treatment initiation is less than 1.1 points per month).

Thus, the invention relates to an inhibitor of at least one tyrosine kinase selected from c-Kit, Lyn, Fyn, PDGFR and CSF1R, or any combination thereof, preferably masitinib or a pharmaceutically acceptable salt or solvate thereof, for use in the treatment of patients suffering from amyotrophic lateral sclerosis (ALS) having a progression of ALSFRS-R score before treatment initiation of less than 1.1 points per month.

In one embodiment, said patients have a progression of ALSFRS-R score before treatment initiation of less than 0.8 points per month. In another embodiment, said patients have a progression of ALSFRS-R score before treatment initiation of less than 1.1 points per month and equal to or greater than 0.8 points per month (≥0.8 to <1.1 points per month).

The invention also aims to solve the technical problem of providing an active ingredient that improves prior art methods for the treatment of non-aggressive or moderately aggressive ALS, more particularly for treating patients with ALS whose progression of ALSFRS-R score before treatment initiation is less than 1.1 points per month.

In one embodiment, said patients have a progression of ALSFRS-R score before treatment initiation of less than 0.8 points per month. In another embodiment, said patients have a progression of ALSFRS-R score before treatment initiation of less than 1.1 points per month and equal to or greater than 0.8 points per month (≥0.8 to <1.1 points per month).

In one embodiment, the tyrosine kinase inhibitor of the invention, or a pharmaceutically acceptable salt or solvate thereof, is an inhibitor of at least one tyrosine kinase selected from c-Kit, Lyn, Fyn, PDGFR and CSF1R, or any combination thereof.

In one embodiment, the tyrosine kinase inhibitor of the invention, or a pharmaceutically acceptable salt or solvate thereof, is an inhibitor of mast cell activity. In another embodiment, the tyrosine kinase inhibitor of the invention, or a pharmaceutically acceptable salt or solvate thereof, is an inhibitor of microglia cell activity. In another embodiment, the tyrosine kinase inhibitor of the invention, or a pharmaceutically acceptable salt or solvate thereof, is an inhibitor of mast cell activity and microglia cell activity.

In one embodiment, the tyrosine kinase inhibitor of the invention, or a pharmaceutically acceptable salt or solvate thereof, is a mast cell inhibitor chosen from the group comprising: masitinib, imatinib, cromolyn sodium, midostaurin, BLU-285, bosutinib, ibrutinib, LAS189386, DP-2618, fostamatinib, nilotinib, dasatinib, sunitinib, axitinib, pazopanib, and toceranib.

In another embodiment, the tyrosine kinase inhibitor of the invention, or a pharmaceutically acceptable salt or solvate thereof, is a microglia cell inhibitor chosen from the group comprising: masitinib, GW2580, pexidartinib, BLZ945, linifanib, OSI-930, imatinib, sunitinib, nilotinib, pazopanib, emactuzumab, FPA008, quizartinib, axitinib, motesanib, cediranib, JNJ-28312141, Ki-20227, MLN-518, sorafenib, and SU-14813.

In one embodiment, the tyrosine kinase inhibitor of the invention, or a pharmaceutically acceptable salt or solvate thereof, is a 2-aminoarylthiazole derivative, or a pharmaceutically acceptable salt or solvate thereof. In one embodiment, said tyrosine kinase inhibitor, or a pharmaceutically acceptable salt or solvate thereof, is masitinib or a pharmaceutically acceptable salt or solvate thereof. In one embodiment, said tyrosine kinase inhibitor or a pharmaceutically acceptable salt or solvate thereof is masitinib mesilate.

The present invention thus relates to a method for the treatment of non-aggressive or moderately aggressive ALS, especially non-aggressive or moderately aggressive ALS defined as a progression of ALSFRS-R score before treatment initiation of less than 1.1 points per month, wherein said method comprises administering to a human patient in need thereof, masitinib or a pharmaceutically acceptable salt or solvate thereof.

In one embodiment, the method of the invention is for the treatment of patients having a progression of ALSFRS-R score before treatment initiation of less than 0.8 points per month. In another embodiment, the method of the invention is for the treatment of patients having a progression of ALSFRS-R score before treatment initiation of less than 1.1 points per month and equal to or greater than 0.8 points per month (≥0.8 to <1.1 points per month).

In one embodiment, the tyrosine kinase inhibitor of the invention, or a pharmaceutically acceptable salt or solvate thereof, is administered in combination with at least one pharmaceutically active ingredient. Said pharmaceutically active ingredient is preferably active in the treatment of ALS. Said pharmaceutically active ingredient is preferably an antiglutamate compound, especially riluzole (6-(trifluoromethoxy)benzothiazol-2-amine); topiramate (2,3:4,5-Bis-O-(1-methylethylidene)-beta-D-fructopyranose sulfamate); gabapentin (2-[1-(aminomethyl)cyclohexyl]acetic acid); lamotrigine (6-(2,3-dichlorophenyl)-1,2,4-triazine-3,5-diamine); talampanel ((8R)-7-Acetyl-5-(4-aminophenyl)-8,9-dihydro-8-methyl-7H-1,3-dioxolo[4,5-h] [2,3]benzodiazepine); ceftriaxone ((6R,7R)-7-[[(2Z)-2-(2-amino-1,3-thiazol-4-yl)-2-methoxyiminoacetyl]amino]-3-[(2-methyl-5,6-dioxo-1H-1,2,4-triazin-3-yl)sulfanylmethyl]-8-oxo-5-thia-1-azabicyclo[4.2.0]oct-2-ene-2-carboxylic acid); an inhibitor of glutamate carboxypeptidase II. Preferably said other pharmaceutically active ingredient is riluzole.

The invention aims to provide an efficient treatment non-aggressive or moderately aggressive ALS at an appropriate dose, route of administration and daily intake.

In one embodiment said tyrosine kinase inhibitor or a pharmaceutically salt or solvate thereof, preferably masitinib or a pharmaceutically acceptable salt or solvate thereof, and more preferably masitinib mesilate, is administered orally.

In one embodiment said tyrosine kinase inhibitor or a pharmaceutically salt or solvate thereof, preferably masitinib or a pharmaceutically acceptable salt or solvate thereof, and more preferably masitinib mesilate, is administered twice a day (i.e. in two daily intakes).

In one embodiment, the tyrosine kinase inhibitor of the invention, or a pharmaceutically salt or solvate thereof, preferably masitinib or a pharmaceutically acceptable salt or solvate thereof, and more preferably masitinib mesilate, is administered at a daily dose ranging from about 1.0 to about 9.0 mg/kg (mg per kilo body weight). In another embodiment, the tyrosine kinase inhibitor of the invention or a pharmaceutically salt or solvate thereof, preferably masitinib or a pharmaceutically acceptable salt or solvate thereof, and more preferably masitinib mesilate, is administered at a dose of 1.5, 3.0, 4.5, 6.0, or 7.5 mg/kg, more preferably at a dose of 3.0, 4.5 or 6 mg/kg/day (mg per kg bodyweight per day).

In one embodiment, the tyrosine kinase inhibitor of the invention, or a pharmaceutically acceptable salt or solvate thereof, is administered at an initial dose of 3.0 mg/kg/day during at least 4 weeks, then 4.5 mg/kg/day during at least 4 weeks, and at 6.0 mg/kg/day thereafter, with each dose escalation being subjected to toxicity controls.

The present invention also relates to a tyrosine kinase inhibitor or a pharmaceutically acceptable salt or solvate thereof for use in the treatment of non-aggressive or moderately aggressive ALS human patients whose progression of ALSFRS-R score before treatment initiation is less than 1.1 points per month as described hereinabove, wherein said tyrosine kinase inhibitor or a pharmaceutically acceptable salt or solvate thereof is masitinib mesilate.

In one embodiment, said patients have a progression of ALSFRS-R score before treatment initiation of less than 0.8 points per month. In another embodiment, said patients have a progression of ALSFRS-R score before treatment initiation of less than 1.1 points per month and equal to or greater than 0.8 points per month (≥0.8 to <1.1 points per month).

In one embodiment, said tyrosine kinase inhibitor is administered in combination with said at least one pharmaceutically active ingredient in a combined preparation for simultaneous, separate, or sequential use.

The invention also relates to a tyrosine kinase inhibitor, preferably masitinib, or a pharmaceutically acceptable salt or solvate thereof, as defined according to the present invention, for use in a treatment of non-aggressive or moderately aggressive ALS.

The invention also relates to a tyrosine kinase tyrosine, preferably masitinib, or a pharmaceutically acceptable salt or solvate thereof, as defined according to the present invention, for use in a treatment of non-aggressive or moderately aggressive ALS, in combination with at least pharmaceutically active ingredient, preferably an antiglutamate compound, especially riluzole; topiramate; gabapentin; lamotrigine; talampanel; ceftriaxone; an inhibitor of glutamate carboxypeptidase II, preferably said other pharmaceutically active ingredient is riluzole.

The invention also relates to a pharmaceutical composition or a medicament or a kit comprising an inhibitor of at least one tyrosine kinase selected from c-Kit, Lyn, Fyn, PDGFR and CSF1R, or any combination thereof, preferably masitinib or a pharmaceutically salt or solvate thereof, for use in a method for the treatment of non-aggressive or moderately aggressive ALS as defined according to the present invention.

In one embodiment, the pharmaceutical composition or the medicament or the kit of the invention also comprises at least one other pharmaceutically active ingredient, preferably an antiglutamate compound, especially riluzole; topiramate; gabapentin; lamotrigine; talampanel; ceftriaxone; an inhibitor of glutamate carboxypeptidase II, preferably said other pharmaceutically active ingredient is riluzole.

The invention also relates to the use of a tyrosine kinase inhibitor, preferably masitinib or a pharmaceutically acceptable salt or solvate thereof, for the preparation of a medicament, or a pharmaceutical composition, for the treatment of non-aggressive or moderately aggressive ALS, optionally in combination with at least one other pharmaceutically active ingredient, preferably an antiglutamate compound, especially riluzole; topiramate; gabapentin; lamotrigine; talampanel; ceftriaxone; an inhibitor of glutamate carboxypeptidase II, preferably said other pharmaceutically active ingredient is riluzole, as defined according to the invention.

The tyrosine kinase inhibitor and the optional at least one pharmaceutically active ingredient, are administered in a dosage regimen that comprises a therapeutically effective amount.

Definitions

In the present invention, the following terms have the following meanings:

As disclosed above, the expression "ALS patients whose rate of progression in ALSFRS-R score prior to treatment initiation is <1.1 points per month" as used in the present application, encompasses a subpopulation of patients from the overall ALS patient population.

The term "ALSFRS-R score" means the revised Amyotrophic Lateral Sclerosis Functional Rating Scale. ALSFRS-R is a score from 0-48 assessing disability. The ALSFRS-R includes 12 questions, each being rated on a five-point scale from 0=cannot do, to 4=normal ability. Individual item scores are summed to produce a reported score of between 0=worst and 48=best. ALSFRS-R scores correlate significantly with quality of life as measured by the Sickness Impact Profile, indicating that the quality of function is a strong determinant of quality of life in ALS. [Cedarbaum J M. The ALSFRS-R: a revised ALS functional rating scale that incorporates assessments of respiratory function. BDNF ALS Study Group (Phase III). J Neurol Sci 1999; 169: 13-21].

The term "progression of ALSFRS-R score" means the rate of change in ALSFRS-R score prior to treatment initiation expressed in points per unit of time (e.g. months). As the disease progresses, the ALSFRS-R score decreases, i.e. the rate of change in ALSFRS-R score is a loss of points.

"Progression of ALSFRS-R score" (point/month) is defined from the date of first ALS-related symptom to time of first treatment (baseline). In other words, in one embodiment, progression of ALSFRS-R score before treatment initiation corresponds to the rate of change of ALSFRS-R score from the date of first ALS-related symptom to time of first treatment (baseline). In the event that ALSFRS-R score at date of first ALS-related symptom is unknown an acceptable estimator is to substitute the upper value of 48 (least disease burden).

The term "baseline" means the time immediately prior to treatment initiation or randomization onto a study.

Calculation of "progression of ALSFRS-R score" for a given ALS patient is performed using the following formula: {(ALSFRS-R score at date of first ALS-related symptom)−(ALSFRS-R score at baseline)} divided by {(time between first ALS-related symptom and baseline)}. In the event that ALSFRS-R score at date of first ALS-related symptom is unknown an acceptable estimator is to substitute the upper value of 48 (least disease burden).

The term "normal progressor" or "non-aggressive or moderately aggressive ALS" means a patient whose progression of ALSFRS-R score before treatment initiation is less than 1.1 points per month. Therefore, "normal progressors" or patients suffering from non-aggressive or moderately aggressive ALS have an ALSFRS-R score that decreases by less than 1.1 points per month. Among the "normal progressors" or patients suffering from non-aggressive or moderately aggressive ALS, it is possible to further distinguish:

patients suffering from non-aggressive ALS with an ALSFRS-R score that decreases by less than 0.8 points per month (<0.8 points per month), and patients suffering from moderately aggressive ALS with an ALSFRS-R score that decreases by is less than 1.1 points per month and equal to or greater than 0.8 points per month (≥0.8 to <1.1 points per month).

Both patients suffering from non-aggressive ALS and patients suffering from moderately aggressive ALS are ALS patients whose progression in ALSFRS-R prior to treatment initiation is <1.1 points per month. In other words, ALS patients whose rate of progression in ALSFRS-R score prior to treatment initiation is <1.1 points per month encompass both patients suffering from non-aggressive ALS and patients suffering from moderately aggressive ALS.

The term "non-aggressive ALS" means a patient whose progression of ALSFRS-R score before treatment initiation is less than 0.8 points per month. Therefore, non-aggressive ALS patients have an ALSFRS-R score that decreases by less than 0.8 points per month.

The term "moderately aggressive ALS" means a patient whose progression of ALSFRS-R score before treatment initiation is less than 1.1 points per month and equal to or greater than 0.8 points per month (≥0.8 to <1.1 points per month). Therefore, moderately aggressive ALS patients have an ALSFRS-R score that decreases by less than 1.1 points per month and equal to or greater than 0.8 points per month (≥0.8 to <1.1 points per month).

The term "fast progressor" or "aggressive ALS" means a patient whose progression of ALSFRS-R score before treatment initiation is equal to or greater than 1.1 points per month. Therefore "fast progressors" or patients suffering from aggressive ALS have an ALSFRS-R score that decreases by 1.1 points or more per month.

The term "ALS patients whose progression in ALSFRS-R prior to treatment initiation is <1.1 points per month" may be used interchangeably with the expression "ALS patients whose rate of progression in ALSFRS-R prior to treatment initiation is <1.1 points per month".

The term "FVC" means the forced vital capacity. FVC (percent of predicted normal) is the vital capacity (VC) measured when the patient is exhaling with maximal speed and effort. The VC can be measured using conventional spirometers that have had a calibration check prior to testing.

The term "CAFS" means the Combined Assessment of Function and Survival (Berry J D et al., The Combined Assessment of Function and Survival (CAFS): a new endpoint for ALS clinical trials. Amyotroph Lateral Scler Frontotemporal Degener. 2013 April; 14(3):162-8.

The term "overall survival" is defined as the time from randomization onto a clinical trial to the time of the documented death.

The term "tracheostomy free survival" is defined as the time from randomization onto a clinical trial to the date of documented death or first tracheotomy.

The term "subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of ALS.

The terms "treating" or "treatment" refers to both therapeutic treatment and prophylactic or preventative measures; wherein the object is to prevent or slow down (lessen) non-aggressive or moderately aggressive ALS. Those in need of treatment include those already with non-aggressive or moderately aggressive ALS as well as those prone to have non-aggressive or moderately aggressive ALS or those in whom non-aggressive or moderately aggressive ALS is to be prevented. A subject is successfully "treated" for non-aggressive or moderately aggressive ALS if, after receiving a therapeutic amount of a tyrosine kinase inhibitor according to the methods of the present invention, the subject shows observable and/or measurable relief to some extent, of one or more of the symptoms associated with non-aggressive or moderately aggressive ALS; reduced morbidity and mortality, and improvement in quality of life issues. The above parameters for assessing successful treatment and improvement in the disease are readily measurable by routine procedures familiar to a physician.

The term "masitinib" designates also an acceptable salt or solvate thereof, especially masitinib mesilate, even when not explicitly stated.

The term "as defined according to the invention" refers to any embodiments or aspects of the invention alone or in combination without limitation, including any preferred embodiments and variants, including any embodiments and features relating to tyrosine kinase inhibitor, preferably masitinib, the method of treatment of non-aggressive or moderately aggressive ALS, pharmaceutical compositions and any combination with other pharmaceutically active ingredient(s), preferably riluzole.

The term "therapeutically effective amount" means the level or amount of agent that is aimed at, without causing significant negative or adverse side effects to the target, (1) delaying or preventing the onset of non-aggressive or moderately aggressive ALS; (2) slowing down or stopping the progression, aggravation, or deterioration of one or more symptoms of non-aggressive or moderately aggressive ALS; (3) bringing about ameliorations of the symptoms of ALS; (4) reducing the severity or incidence of non-aggressive or moderately aggressive ALS; or (5) curing non-aggressive or moderately aggressive ALS. A therapeutically effective amount may be administered prior to the onset of non-aggressive or moderately aggressive ALS, for a prophylactic or preventive action. Alternatively or additionally, the therapeutically effective amount may be administered after initiation of non-aggressive or moderately aggressive ALS, for a therapeutic action or maintenance of a therapeutic action.

The term "pharmaceutically acceptable carrier or excipient" refers to an excipient or carrier that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, injected preparations should meet sterility, pyrogenicity, general safety and purity standards as required by regulatory offices, such as, for example, FDA Office or EMA.

The term "solvate" is used herein to describe a molecular complex comprising the compound of the invention and one or more pharmaceutically acceptable solvent molecules.

The term "about" preceding a figure means plus or less 10% of the value of said figure.

As used herein, the term an "aryl group" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. In one embodiment, the aryl group is a monocyclic ring, wherein the ring comprises 6 carbon atoms, referred to herein as "$(C_6)$aryl".

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo [2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

The term "heterocycle" as used herein, refers collectively to heterocycloalkyl groups and heteroaryl groups.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O)NR$_{11}$R$_{12}$, —NR$_{13}$C(O)R$_{14}$, a halo, —OR$_{13}$, cyano, nitro, a haloalkoxy, —C(O)R$_{13}$, —NR$_{11}$R$_{12}$, —SR$_{13}$, —C(O)OR$_{13}$, —OC(O)R$_{13}$, —NR$_{13}$C(O)NR$_{11}$R$_{12}$, —OC(O)NR$_{11}$R$_{12}$, —NR$_{13}$C(O)OR$_{14}$, —S(O)rR$_{13}$, —NR$_{13}$S(O)rR$_{14}$, —OS(O)rR$_{14}$, S(O)rNR$_{11}$R$_{12}$, —O, —S, and —N—R$_{13}$, wherein r is 1 or 2; R$_{11}$ and R$_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R$_{11}$ and R$_{12}$ taken together with the nitrogen to which they are attached is optionally substituted heterocycloalkyl or optionally substituted heteroaryl; and R$_{13}$ and R$_{14}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl. In certain embodiments, the term "substituent" or the adjective "substituted" refers to a solubilizing group.

The term "solubilizing group" means any group which can be substantially ionized and that enables the compound to be soluble in a desired solvent, such as, for example, water or water-containing solvent. Furthermore, the solubilizing group can be one that increases the compound or complex's lipophilicity. Typically, the solubilizing group is selected from alkyl group substituted with one or more heteroatoms such as N, O, S, each optionally substituted with alkyl group substituted independently with alkoxy, amino, alkylamino, dialkylamino, carboxyl, cyano, or substituted with cycloheteroalkyl or heteroaryl, or a phosphate, or a sulfate, or a carboxylic acid. For example, by "solubilizing group" it is referred herein to one of the following:

- an alkyl, cycloalkyl, aryl, heretoaryl group comprising either at least one nitrogen or oxygen heteroatom or which group is substituted by at least one amino group or oxo group;
- an amino group which may be a saturated cyclic amino group which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl;
- one of the structures a) to i) shown below, wherein the wavy line and the arrow line correspond to the point of attachment to core structure of formula [A].

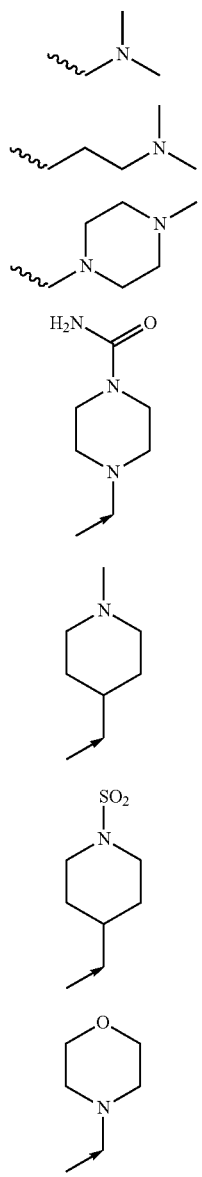

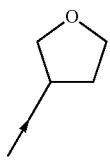

h

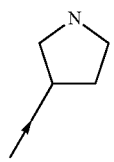

i

The term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

The term "halogen" means —F, —Cl, —Br or —I.

DETAILED DESCRIPTION

The present invention therefore relates to a method for treating non-aggressive or moderately aggressive amyotrophic lateral sclerosis (ALS) in a subject preferably in a human patient, comprising administering a tyrosine kinase inhibitor, or a pharmaceutically acceptable salt or solvate thereof, to subjects or patients in need thereof. Preferably, a therapeutically effective amount of a tyrosine kinase inhibitor, or a pharmaceutically acceptable salt or solvate thereof, is administered to the subject.

In one embodiment, non-aggressive or moderately aggressive ALS in a patient is diagnosed through the calculation of the ALSFRS-R score for said patient. Calculation of progression of ALSFRS-R score for a given ALS patient is performed using the following formula: {(ALSFRS-R score at date of first ALS-related symptom)−(ALSFRS-R score at baseline)} divided by {(time between first ALS-related symptom and baseline)}. In the event that ALS-FRS-R score at date of first ALS-related symptom is unknown an acceptable estimator is to substitute the upper value of 48 (least disease burden).

Thus, in one embodiment, the progression of ALSFRS-R score before treatment initiation corresponds to the rate of change of ALSFRS-R score from the date of first ALS-related symptom to time of first treatment (baseline).

Patients whose progression of ALSFRS-R score before treatment initiation is less than 1.1 points per month suffer from non-aggressive or moderately aggressive ALS and are defined as "normal progressors". Thus, "normal progressors", i.e. patients whose progression of ALSFRS-R score before treatment initiation is less than 1.1 points per month (<1.1 points per month) encompass:

- patients suffering from non-aggressive ALS whose progression of ALSFRS-R score before treatment initiation is less than 0.8 points per month (<0.8 points per month), and
- patients suffering from moderately aggressive ALS whose progression of ALSFRS-R score before treatment initiation is less than 1.1 points per month and equal to or greater than 0.8 points per month (≥0.8 to <1.1 points per month).

Thus, in one embodiment, non-aggressive or moderately aggressive ALS is defined as a progression of ALSFRS-R score before treatment initiation of less than 1.1 points per month. In another embodiment, non-aggressive or moderately aggressive (ALS) is defined as a rate of change of ALSFRS-R score from the date of first ALS-related symptom to time of first treatment (baseline) of less than 1.1 points per month.

In one embodiment, non-aggressive ALS is defined is defined as a progression of ALSFRS-R score before treatment initiation of less than 0.8 points per month. In another embodiment, non-aggressive ALS is defined as a rate of change of ALSFRS-R score from the date of first ALS-related symptom to time of first treatment (baseline) of less than 0.8 points per month.

In one embodiment, moderately aggressive ALS is defined is defined as a progression of ALSFRS-R score before treatment initiation of less than 1.1 points per month and equal to or greater than 0.8 points per month (≥0.8 to <1.1 points per month). In another embodiment, moderately aggressive ALS is defined as a rate of change of ALSFRS-R score from the date of first ALS-related symptom to time of first treatment (baseline) of less than 1.1 points per month and equal to or greater than 0.8 points per month (≥0.8 to <1.1 points per month).

In the event that ALSFRS-R score at date of first ALS-related symptom is unknown an acceptable estimator is to substitute the upper value of 48 (least disease burden).

ALSFRS-R is a score from 0-48 assessing disability. The ALSFRS-R includes 12 questions, each being rated on a five-point scale from 0=cannot do, to 4=normal ability. Individual item scores are summed to produce a reported score of between 0=worst and 48=best. ALSFRS-R scores correlate significantly with quality of life as measured by the Sickness Impact Profile, indicating that the quality of function is a strong determinant of quality of life in ALS. [Cedarbaum J M. J Neurol Sci 1999; 169:13-21].

The ALSFRS-R is a quickly administered (5 minute) ordinal rating scale (ratings 0-4) used to determine subjects' assessment of their capability and independence in 12 functional activities/questions. All 12 activities are relevant in ALS. Initial validity was established by documenting that in ALS patients, change in ALSFRS-R scores correlated with change in strength over time, and was closely associated with quality of life measures, and predicted survival [Traynor B, et al., Neurology, 2004. 63:1933-35]. The test-retest reliability is greater than 0.88 for all test items. The advantages of the ALSFRS-R are that the categories are relevant to ALS, the instrument is a sensitive and reliable tool for assessing activities of daily living function in patients with ALS, and it is quickly administered. With appropriate training the ALSFRS-R can be administered with high inter-rater reliability and test/retest reliability.

The ALSFRS-R 12 questions and their rating scales are described below:

ALSFRS-R Instrument
1. Speech
Ask if subject notes a change in speech. The subject is to compare his/her current function with function prior to any symptoms of ALS.
4 Normal speech process
  Speech is as it was prior to onset of illness; rate 4 if subject notes completely normal speech
3 Detectable speech disturbance
  Some detectable alteration in speech
2 Intelligible with repeating
  Some repetition is required to understand the speech
1 Speech combined with non-vocal communication
  Speech combined with gestures, including hand gestures or head nodding, or communication aids, including low or high technical devices, are required to communicate
0 Loss of useful speech
  Impossible for subject to communicate verbally 2. Salivation
Rate current status versus prior to ALS onset regardless of whether subject is taking medication for salivation. Current status includes all medications or therapies used.
4 Normal
3 Slight but definite excess of saliva in mouth; may have night time drooling
2 Moderately excessive saliva; may have minimal drooling
1 Marked excess of saliva with some drooling
0 Marked drooling
  Requires constant tissue or handkerchief
3. Swallowing
4 Normal eating habits
  No difficulty swallowing, can eat any foods or liquids of choice
3 Early eating problems—occasional choking
  Ask whether subject avoids any foods because they get caught in his/her throat; can still eat all foods of choice but with occasional choking
2 Dietary consistency changes
  Avoids certain foods or requires that consistency of foods be changed
1 Needs supplemental tube feeding
0 NPO
  Exclusively parenteral or enteral feeding
4. Handwriting
Question asks about writing with dominant hand prior to ALS onset without any assistive devices, such as foam tubing and/or mechanical aids due to hand or finger weakness.
4 Normal
3 Slow or sloppy: all words are legible
2 Not all words are legible
1 No words are legible, but can still grip pen
0 Unable to grip pen
5a. Cutting Food and Handling Utensils
in patients without gastrostomy
Note: Use 5b if >50% of nutrition is through g-tube
If the subject chooses not to cut the food or feed self for whatever reason, he/she is to be rated as not able. Not able is rated as 0.
4 Normal
  No difficulty cutting or handling utensils by methods used prior to disease onset
3 Somewhat slow and clumsy, but no help needed
  Some difficulty cutting or handling utensils by methods used prior to disease onset but subject continues to do so independently
2 Can cut most foods (>50%), although slow and clumsy; some help needed
  Some difficulty cutting or handling utensils by methods used prior to disease onset; subject requires assistance, but still tries to cut some foods, and still does >50% of the task successfully
1 Food must be cut by someone, but can still feed slowly
  Patient cannot cut foods by methods used prior to disease onset, but still tries to feed him/herself and succeeds at least occasionally
0 Needs to be fed
5b. Cutting Food and Handling Utensils
in patients with gastrostomy
Note: 5b option is used if the subject has a gastrostomy and only if it is the primary method of eating. If the subject has a gastrostomy proactively, but receives most of their nutrients orally (more than 50%) then use 5a, until 5b is the appropriate choice. The responses to question 5b refer to tube feeding procedures and manipulations.
4 Normal
3 Clumsy, but able to perform all manipulations independently
2 Some help needed with closures and fasteners
1 Provides minimal assistance to caregiver
0 Unable to perform any aspect of task
6. Dressing and Hygiene
If the subject chooses not to dress or bathe self for whatever reason he/she is rated as not able. Not able is rated as 0.
4 Normal function
Patient has no difficulty, and is still completely independent in dressing and hygiene by methods used prior to disease onset
3 Independent; Can complete self-care with effort or decreased efficiency
Patient still completely independent in dressing but requires more effort to dress; no substitute methods are used to dress
2 Intermittent assistance or substitute methods
Patient requires occasional assistance or the use of assistive devices or substitute methods (e.g., pull-on clothes, Velcro closures or shoes, pre-buttoned shirt, lying down to don pants, using a shower chair or bench) in dressing and hygiene. Methods used are now different than those used prior to disease onset
1 Needs attendant for self-care
Means subject needs daily caregiver assistance with dressing but subject has some level of function
0 Total dependence
7. Turning in Bed and Adjusting Bed Clothes
If the subject chooses not to turn in bed or adjust bed clothes for whatever reason, he/she is rated as not able. The ability to do both activities, turning and adjusting bedclothes, to be rated 3 or 4. Performing one activity is rated 2.
4 Normal function
3 Somewhat slow and clumsy, but no help needed
Patient may use bedrail, headboard or electric bed.
2 Can turn alone, or adjust sheets, but with great difficulty
Patient can turn alone or adjust sheets, but completes task with great difficulty; no help needed. Patient may use bedrail, headboard or electric bed.
1 Can initiate, but not turn or adjust sheets alone
0 Helpless
8. Walking
Definition of walking as defined by subject.
4 Normal
3 Early ambulation difficulties
Notes some difficulty, but walks without assistance
2 Walks with assistance
Includes AFO, cane, walker, or a caregiver
1 Non-ambulatory functional movement only
Patient is able to move lower extremities partially for functional movement; able to stand and bear weight for transfers, but unable to walk
0 No purposeful leg movement
9. Climbing Stairs
If the subject chooses not to climb stairs for whatever reason, he/she is rated as "0—Cannot do".
4 Normal
3 Slow
2 Mild unsteadiness or fatigue
Patient needs to rest between steps, or feels unsteady, but does not need rail 1 Needs assistance
Patient needs assistance including handrail or caregiver; assistance is needed for stability and safety
0 Cannot do
ALSFRS-R Respiratory Subscale
10. Dyspnea
4 None
3 Occurs when walking
2 Occurs with one or more of the following: eating, bathing, dressing
1 Occurs at rest: difficulty breathing when either sitting or lying
0 Significant difficulty: considering using mechanical respiratory support
11. Orthopnea
Rate 0 if using nocturnal BiPAP and subject NEVER sleeps without device. If subject uses BiPAP, but sometimes sleeps without it (is able to sleep without it), select the number that best describes the subject's orthopnea when sleeping without device.
4 None
3 Some difficulty sleeping at night due to shortness of breath, does not routinely use more than two pillows
2 Needs extra pillows in order to sleep (more than two)
1 Can only sleep sitting up
0 Unable to sleep without mechanical assistance
12. Respiratory Insufficiency
4 None
3 Intermittent use of BiPAP
2 Continuous use of BiPAP during the night
1 Continuous use of BiPAP during day & night
0 Invasive mechanical ventilation by intubation or tracheostomy Hence, there exist at least two highly distinct subpopulations of ALS patient within the overall ALS population, which can be distinguished from one another in terms of 'fast progressor' patients (referred to also as 'aggressive ALS') whose progression of ALSFRS-R score before treatment initiation is equal to or greater than 1.1 points per month; and 'normal progressor' patients (referred to also as 'non-aggressive or moderately aggressive ALS') whose progression of ALSFRS-R score before treatment initiation is less than 1.1 points per month. The former subgroup represents a more aggressive and heterogeneous form of disease with patients at higher risk of death (significantly shorter median survival time) or tracheostomy [Kimura F, et al. Neurology 2006; 66:265-267]. Among the "normal progressors" or patients suffering from non-aggressive or moderately aggressive ALS, it is possible to further distinguish:
patients suffering from non-aggressive ALS with an ALSFRS-R score that decreases by less than 0.8 points per month (<0.8 points per month), and
patients suffering from moderately aggressive ALS with an ALSFRS-R score that decreases by is less than 1.1 points per month and equal to or greater than 0.8 points per month (≥0.8 to <1.1 points per month).

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation. Within the meaning of the present invention, a "tyrosine kinase inhibitor" is thus a drug that inhibits tyrosine kinases, thereby interfering with signaling processes within cells. Blocking such processes can stop the cell growing and dividing.

In one embodiment, the tyrosine kinase inhibitor or a pharmaceutically acceptable salt or solvate thereof for use in the method for treating non-aggressive or moderately aggressive ALS in a subject of the invention is an inhibitor of wild-type c-Kit, Lyn, Fyn, PDGFR and CSF1R kinase activity, or any combination thereof. In another embodiment, the tyrosine kinase inhibitor of the invention, or a pharmaceutically acceptable salt or solvate thereof, inhibits wild-type c-Kit, Lyn, Fyn, PDGFR and/or CSF1R without inhibiting, at therapeutic doses, kinases associated with known toxicities (i.e. those tyrosine kinases or tyrosine kinase receptors attributed to possible tyrosine kinase inhibitor cardiac toxicity, including ABL, KDR and Src) [Dubreuil et al., 2009, PLoS ONE 2009. 4(9):e7258] [Davis et al., Nat Biotechnol 2011, 29(11): 1046-51].

In one embodiment, the tyrosine kinase inhibitor or a pharmaceutically acceptable salt or solvate thereof for use in the method of the present invention is thus capable of inducing cell cycle arrest and apoptosis of cell lines dependent on c-Kit signaling [Dubreuil et al., 2009, PLoS ONE, 4(9):e7258]. Stem cell factor, the ligand of the c-Kit receptor, is a critical growth factor for mast cells; thus, the tyrosine kinase inhibitor or a pharmaceutically acceptable salt or solvate thereof for use in the method of the present invention is an effective anti-mastocyte, exerting a direct antiproliferative and pro-apoptotic action on mast cells through its inhibition of c-Kit signaling. Similarly, Lyn and Fyn kinases are known to play the role of key components of the transduction pathway leading to IgE induced degranulation of mast cells; thus, the tyrosine kinase inhibitor or a pharmaceutically acceptable salt or solvate thereof for use in the method of the present invention also regulates the activation of mast cells through its targeting of Lyn and Fyn.

Mast cells play an important role in sustaining the inflammatory network of the central nervous system in their own right, with mast cell-microglia cross talk further contributing to sustaining the inflammatory response.

Mast cells are characterized by their heterogeneity, not only regarding tissue location and structure but also at functional and histochemical levels. Mast cell activation is followed by the controlled release of a variety of mediators that are essential for the defense of the organism against invading pathogens. Mast cells produce a large variety of mediators categorized here into three groups:

- Preformed granule-associated mediators (histamines, proteoglycans, and neutral proteases);
- Lipid-derived mediators (prostaglandins, thromboxanes and leucotrienes);
- Various cytokines (including the interleukins: IL-1, IL-2, IL-3, IL-4, IL-5, IL-6, IL-8 and tumor necrosis factor alpha TNF-α, GM-CSF, MIP-1α, MIP-1β and IFN-γ).

Human mast cells constitutively express a number of receptors for different biological molecules. Among these receptors, whose ligation induces the activation of mast cells, the best known is the high affinity receptor for IgE (FcεRI). Binding of IgE-multivalent antigen complexes to FcεRI leads to receptor aggregation and internalization, signaling, and degranulation. This can be accompanied by the transcription of cytokine genes, thus, perpetuating the inflammatory response. Moreover, triggering of mast cells leads to the secretion of diverse pre-formed and/or de novo synthesized mediators, such as vasoactive amines (histamine, serotonin), sulfated proteoglycans, lipid mediators (prostaglandin D2, leucotrienes), growth factors, proteases, cytokines and chemokines as described previously. These mediators can, alone or in synergy with macrophage-derived derived and T cell-derived cytokines, generate a complex inflammatory response and induce the recruitment and activation of inflammatory cells to the site of degranulation.

Mast cells are found on both sides of the BBB and also have the ability to rapidly cross the BBB, thereby increasing their numbers in response to physiological stimuli [Nautiyal K, et al. Proc Natl Acad Sci USA. 2008 November; 18; 105(46): 18053-18057] [Theoharides T C, et al. J Neuroimmunol. 2004 January; 146(1-2):1-12] [Silverman A J, et al. J Neurosci 2000, 20:401-408]. Release of these proinflammatory mediators into the central nervous system can alter the function of both neural and vascular elements [Skaper S D, et al. Immunol 2014; 141:314-327]. Stem cell factor, the ligand of the c-Kit receptor, is a critical growth factor for mast cells. Similarly, Lyn and Fyn kinases are known to play the role of key components of the transduction pathway leading to IgE induced degranulation of mast cells; thus, c-Kit, Lyn and Fyn are targets for regulating mast cell activity.

Thus, in one embodiment, the tyrosine kinase inhibitor of the invention, or a pharmaceutically acceptable salt or solvate thereof, is an inhibitor of mast cell activity.

In one embodiment, said inhibitor of mast cell activity is imatinib (STI571, Novartis), more preferably imatinib mesilate. Therefore, in a particular embodiment, the invention relates to a method for the treatment of non-aggressive or moderately aggressive ALS in a mammal, and especially a human patient, comprising the administration of an effective amount of the compound known in the art as imatinib (STI571, CGP57148B): 4-[(4-Methyl-1-piperazinyl) methyl]-N-(4-methyl-3-[4-(3-pyridinyl)-2-pyrimidinyl] aminolphenyl)benzamide. The preparation of this compound is described in example 21 of EP 564 409 and the form, which is particularly useful is described in WO 99/03854.

In another embodiment, the inhibitor of mast cell activity can be selected from: midostaurin (PKC412; Novartis), dasatinib (BMS354825; Bristol-Myers Squibb), sunitinib (SU11248; Pfizer), nilotinib (AMN107; Novartis), axitinib (AG013736; Pfizer), pazopanib (GlaxoSmithKline), toceranib (SU11654; Pfizer), BLU-285 (Blueprint Medicines), bosutinib (SKI-606; Pfizer), ibrutinib (PCI-32765; Pharmacyclics), LAS189386 (Almirall R&D Center), DP-2618 (Deciphera Pharmaceuticals), fostamatinib (R788; Rigel), and cromolyn sodium.

In another embodiment, the inhibitor of mast cell activity can be selected from: masitinib, imatinib, cromolyn sodium, midostaurin, BLU-285, bosutinib, ibrutinib, LAS189386, DP-2618, fostamatinib, nilotinib, dasatinib, sunitinib, axitinib, pazopanib, and toceranib.

Neuron derived CSF-1 via CSF-1R has been recognized as a mechanism to trigger microglia proliferation in the spinal cord. It has been observed that damaged motoneurons induce the expansion of spinal cord microglia by expressing CSF-1 [Guan Z, et al. (2016) Nature Neuroscience 19(1): 94-101]; thus, CSF-1R is a target for regulating microglia activity. Furthermore, microglia respond to pro-inflammatory signals released from non-neuronal cells, mainly those of immune origin such as mast cells. Evidence indicates that there is extensive communication between the immune system and the central nervous system, with proinflammatory cytokines playing a key role in this communication [Skaper S D, et al. Immunol 2014; 141:314-327]. Hence, this mast cell-microglia cross talk further intensifies and prolongs the effects of chronic neuroinflammation.

The tyrosine kinase inhibitor or a pharmaceutically acceptable salt or solvate thereof for use in the method of the present invention also regulates the activation of microglia cells through its targeting of CSF-1R.

Thus, in one embodiment, the tyrosine kinase inhibitor of the invention, or a pharmaceutically acceptable salt or solvate thereof, is an inhibitor of microglia cell activity.

In one embodiment, said an inhibitor of microglia cell activity can be selected from: GW2580 (GlaxoSmithKline), pexidartinib (PLX3397; Plexxikon), BLZ945 (Novartis), linifanib (ABT-869; Abbott), OSI-930 (OSI Pharmaceuticals Inc), imatinib (STI571, Novartis), sunitinib (SU11248; Pfizer), nilotinib (AMN107; Novartis), pazopanib (GlaxoSmithKline), emactuzumab (RG7155; Roche), FPA008 (Five Prime Therapeutics, Inc), quizartinib (AC220; Daiichi Sankyo), axitinib (AG-013736; Pfizer), motesanib (AMG-706; Takeda), cediranib (AZD-2171; AstraZeneca), JNJ-28312141 (Johnson & Johnson), Ki-20227 (Kirin Pharma Company Limited), MLN-518 (Millennium), Sorafenib (Bayer), and SU-14813 (Pfizer).

In another embodiment, said an inhibitor of microglia cell activity can be selected from: masitinib, GW2580, pexidartinib, BLZ945, linifanib, OSI-930, imatinib, sunitinib, nilotinib, pazopanib, emactuzumab, FPA008, quizartinib, axitinib, motesanib, cediranib, JNJ-28312141, Ki-20227, MLN-518, Sorafenib, and SU-14813.

Furthermore, there is extensive communication between the immune system, via mast cells for example, and the central nervous system, with proinflammatory cytokines playing a key role in this communication [Skaper S D, et al. Immunol 2014; 141:314-327]. Resultant mast cell-microglia cross talk further intensifies and prolongs the effects of chronic neuroinflammation; thus, the tyrosine kinase inhibitor or a pharmaceutically acceptable salt or solvate thereof for use in the method of the present invention also modulates neuroinflammation via inhibition of mast cell-microglia cross talk.

In one embodiment, the tyrosine kinase inhibitor of the invention, or a pharmaceutically acceptable salt or solvate thereof, is an inhibitor of mast cell activity and microglia cell activity.

In one embodiment, the tyrosine kinase inhibitor of the invention, or a pharmaceutically acceptable salt or solvate thereof, is a 2-aminoarylthiazole derivative.

In one embodiment, the tyrosine kinase inhibitor of the invention, or a pharmaceutically acceptable salt or solvate thereof, is a 2-aminoarylthiazole derivative of formula [A]. In another embodiment, the tyrosine kinase inhibitor of the invention, or a pharmaceutically acceptable salt or solvate thereof, is a 2-aminoarylthiazole derivative of formula [B].

In one embodiment, the tyrosine kinase inhibitor for use in the method for treating non-aggressive or moderately aggressive ALS in a subject (i.e. human patient with ALS whose progression of ALSFRS-R score before treatment initiation is less than 1.1 points per month) of the invention has the following formula [A]:

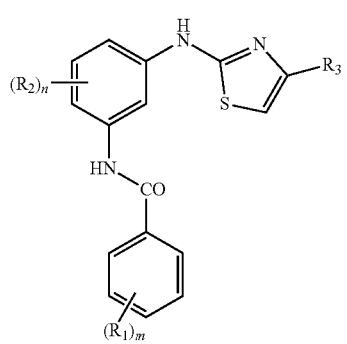

wherein:

$R_1$ and $R_2$, are selected independently from hydrogen, halogen, a linear or branched alkyl, cycloalkyl group containing from 1 to 10 carbon atoms, trifluoromethyl, alkoxy, cyano, dialkylamino, and a solubilizing group, m is 0-5 and n is 0-4; the group $R_3$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;

(ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

or a pharmaceutically acceptable salt or solvate thereof.

In one embodiment, the tyrosine kinase inhibitor for use in the method for treating non-aggressive ALS in a subject (i.e. human patient with ALS whose progression of ALSFRS-R score before treatment initiation is less than 0.8 points per month) of the invention has formula [A] as defined hereinabove.

In one embodiment, the tyrosine kinase inhibitor for use in the method for treating moderately aggressive ALS in a subject (i.e. human patient with ALS whose progression of ALSFRS-R score before treatment initiation is ≥0.8 to <1.1 points per month) of the invention has formula [A] as defined hereinabove.

In a particular embodiment, the tyrosine kinase inhibitor for use in the method for treating non-aggressive or moderately aggressive ALS in a subject (i.e. human patient with ALS whose progression of ALSFRS-R score before treatment initiation is less than 1.1 points per month) of the invention has general formula [B],

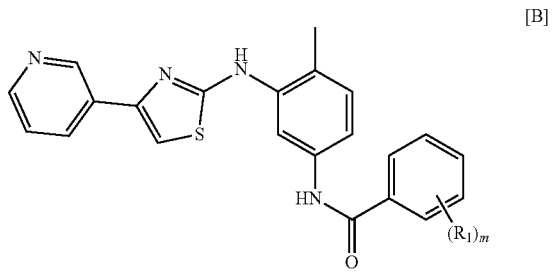

wherein:

$R_1$ is selected independently from hydrogen, halogen, a linear or branched alkyl, cycloalkyl group containing from 1 to 10 carbon atoms, trifluoromethyl, alkoxy, amino, alkylamino, dialkylamino, solubilizing group, and m is 0-5, or a pharmaceutically acceptable salt or solvate thereof.

In a particular embodiment, the tyrosine kinase inhibitor for use in the method for treating non-aggressive ALS in a subject (i.e. human patient with ALS whose progression of ALSFRS-R score before treatment initiation is less than 0.8 points per month) of the invention has general formula [B] as defined hereinabove.

In a particular embodiment, the tyrosine kinase inhibitor for use in the method for treating moderately aggressive ALS in a subject (i.e. human patient with ALS whose progression of ALSFRS-R score before treatment initiation is ≥0.8 to <1.1 points per month) of the invention has general formula [B] as defined hereinabove.

Pharmaceutically acceptable salts preferably are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic, in particular methanesulfonic acid, or aromatic sulfonic acids, for example benzene-, p-toluene- or naphthalene-2-sulfonic acid.

Unless otherwise indicated, references to "mesilate" are used in the present invention to refer to a salt of methanesulfonic acid with a named pharmaceutical substance (such as compounds of formula [A] or [B]). Use of mesilate rather than mesylate is in compliance with the INNM (International nonproprietary names modified) issued by WHO (e.g. World Health Organization (February 2006). *International Nonproprietary Names Modified*. INN Working Document 05.167/3. WHO.). For example, masitinib or imatinib mesilate mean the methanesulfonic acid salt of masitinib and imatinib, respectively.

In one highly preferred embodiment, the tyrosine kinase inhibitor of formula [B] for use in the method of the invention is masitinib or a pharmaceutically acceptable salt or solvate thereof, more preferably masitinib mesilate.

Preferably, "masitinib mesilate" means the orally bioavailable mesilate salt of masitinib—CAS 1048007-93-7 (MsOH); $C_{28}H_{30}N_6OS \cdot CH_3SO_3H$; MW 594.76:

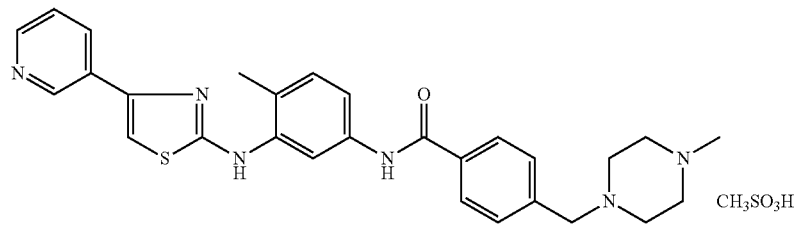

The chemical name for masitinib is 4-(4-methylpiperazin-1-ylmethyl)-N-[4-methyl-3-(4-pyridin-3ylthiazol-2-ylamino) phenyl]benzamide—CAS number 790299-79-5.

Masitinib was described in U.S. Pat. No. 7,423,055 and EP 1 525 200 B1. A detailed procedure for the synthesis of masitinib mesilate is given in WO 2008/098949.

Tyrosine kinase inhibitors, preferably of formula [A] or [B] or masitinib mesilate can preferably be used as an inhibitor of wild-type c-Kit, Lyn, Fyn, PDGFR and CSF1R kinase activity, or any combination thereof.

In connection with the present invention, it would seem without willing to be bound by a theory, that molecules capable of inhibiting the c-Kit/SCF signaling pathway and therefore survival and/or activation of mast cells, or capable of modulating mast cell degranulation and therefore mast cell-microglia cross talk, or capable of inhibiting the CSF-1/CSF-1R signaling pathway and therefore microglia proliferation, or any combination thereof, may be able to control the symptoms and progression of ALS. In connection to the present invention a tyrosine kinase inhibitor, notably as defined above, especially masitinib, through its inhibition of the tyrosine kinase activity of wild-type c-Kit, Lyn, Fyn, PDGFR and CSF1R, is fulfilling this role in the treatment of non-aggressive or moderately aggressive ALS, in particular patient whose progression of ALSFRS-R score before treatment initiation is less than 1.1 points per month, via but not limited to, reducing the overall mast cell burden, inhibiting the global activity of mast cells, inhibiting mast cell-microglia cross talk, and inhibiting microglia proliferation; thus, impacting on the overall inflammatory cascade. Unexpectedly, without willing to be bound by a theory, it is through this multifaceted mechanism of action that the use of a tyrosine kinase inhibitor according to the invention can elicit a response in non-aggressive or moderately aggressive ALS patients.

In one embodiment, said patients have a progression of ALSFRS-R score before treatment initiation of less than 0.8 points per month. In another embodiment, said patients have a progression of ALSFRS-R score before treatment initiation of less than 1.1 points per month and equal to or greater than 0.8 points per month (≥0.8 to <1.1 points per month).

The present invention relates to a method for the treatment of non-aggressive or moderately aggressive ALS in a human patient, wherein said method comprises administering to a human patient in need thereof, a tyrosine kinase inhibitor or a pharmaceutically acceptable salt or solvate thereof, especially masitinib or a pharmaceutically acceptable salt or solvate thereof.

In relation to the present invention, non-aggressive or moderately aggressive ALS in a human patient is defined by a progression of ALSFRS-R score before treatment initiation of less than 1.1 points per month. According to the present invention, non-aggressive ALS in a human patient is further defined by a progression of ALSFRS-R score before treatment initiation of less than 0.8 points per month. According to the present invention, moderately aggressive ALS in a human patient is further defined by a progression of ALSFRS-R score before treatment initiation of less than 1.1 points per month and equal to or greater than 0.8 points per month (≥0.8 to <1.1 points per month).

Thus, the present invention relates to a method for the treatment of patients suffering from amyotrophic lateral sclerosis (ALS) having a progression of ALSFRS-R score before treatment initiation of less than 1.1 points per month.

The invention also relates to an inhibitor of at least one tyrosine kinase selected from c-Kit, Lyn, Fyn, PDGFR and CSF1R, or any combination thereof, preferably masitinib or a pharmaceutically acceptable salt or solvate thereof, for use in the treatment of patients suffering from amyotrophic lateral sclerosis (ALS) having a progression of ALSFRS-R score before treatment initiation of less than 1.1 points per month.

The invention also relates to the use of an inhibitor of at least one tyrosine kinase selected from c-Kit, Lyn, Fyn, PDGFR and CSF1R, or any combination thereof, preferably masitinib or a pharmaceutically acceptable salt or solvate thereof, for the preparation of a medicament for the treatment of patients suffering from amyotrophic lateral sclerosis (ALS) having a progression of ALSFRS-R score before treatment initiation of less than 1.1 points per month.

In one embodiment, said patients have a progression of ALSFRS-R score before treatment initiation of less than 0.8 points per month. In another embodiment, said patients have a progression of ALSFRS-R score before treatment initiation of less than 1.1 points per month and equal to or greater than 0.8 points per month (≥0.8 to <1.1 points per month).

In relation to the present invention, the term "treatment" (and its various grammatical forms) refers to preventing, curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease.

The inventors have surprisingly shown that masitinib provides therapeutic benefit to a highly distinct subpopulation of ALS patients, with progression of ALSFRS-R score before treatment initiation serving as an independent predictor factor for treatment efficacy.

A randomized placebo-controlled phase 3 study (AB10015) was conducted to compare the efficacy and safety of masitinib in combination with riluzole versus placebo in combination with riluzole in the treatment of patients suffering from ALS (see Example 1).

Following a prospectively declared AB10015 study interim analysis the inventors have surprisingly shown that in a subpopulation of ALS, masitinib generates a clinical advantage when compared with placebo (see Example 2). This subpopulation, which is defined with a restricted eligibility criterion, is comprised of ALS patients whose progression of ALSFRS-R score before treatment initiation is less than 1.1 points per month; collectively referred to as the non-aggressive or moderately aggressive ALS subpopulation or 'normal progressor' subpopulation of the overall ALS population, comprising patients suffering from non-aggressive ALS or moderately aggressive ALS as defined hereinabove. This outcome represents new knowledge and could not have been predicted by teachings from the prior art.

Masitinib showed an improvement over placebo in its primary endpoint, (P=0.0032, Table 4), with a statistically significant retardation in rate of disease progression. This positive treatment effect was unexpectedly shown to be strongly driven by the non-aggressive or moderately aggressive ALS (normal progressors) subpopulation (P=0.0004, Table 5), with limited or no masitinib effectiveness in aggressive ALS (faster progressors, or rapid progressors as defined hereinabove) patients when compared with placebo (P=0.4327, Table 6). Taken together, these data demonstrate that masitinib generates a clinical advantage in the restricted population of non-aggressive or moderately aggressive ALS (normal progressors) that is unexpectedly superior to other patient cohorts. These findings support the use of progression of ALSFRS-R score before treatment initiation (with a threshold of less than 1.1 points per month) as an independent predictor factor for masitinib treatment efficacy and patient selection from among the overall ALS population.

The inventors have surprisingly shown therefore that a distinct subpopulation responds to masitinib treatment, with said distinction being made according to aggressiveness of disease as calculated via rate of change of ALSFRS-R score from the date of first ALS-related symptom to time of randomization onto the study (baseline) of less than 1.1 points per month (comprising non-aggressive ALS and moderately aggressive ALS subpopulations as defined hereinabove); which can be generalized as progression of ALSFRS-R score prior to treatment initiation expressed in points per unit of time.

The method of the present invention was advantageously shown to provide a significant beneficial effect on non-aggressive or moderately aggressive ALS patients (normal progressors). In one embodiment, it is considered that the expression "normal progressors" or "non-aggressive or moderately aggressive" actually refers to a clinical situation wherein the treated patients suffering from ALS present with a history of disease progression expressed in terms of progression of ALSFRS-R score of less than 1.1 points per month.

In one embodiment, the tyrosine kinase inhibitor of the invention, or a pharmaceutically acceptable salt or solvate thereof, is administered in combination with at least one pharmaceutically active ingredient. Said pharmaceutically active ingredient is preferably active in the treatment of ALS.

Examples of pharmaceutically active ingredients include, without being limited to, an antiglutamate compound, especially riluzole (6-(trifluoromethoxy)benzothiazol-2-amine); topiramate (2,3:4,5-Bis-O-(1-methylethylidene)-beta-D-fructopyranose sulfamate); gabapentin (2-[1-(aminomethyl) cyclohexyl]acetic acid); lamotrigine (6-(2,3-dichlorophenyl)-1,2,4-triazine-3,5-diamine); talampanel ((8R)-7-Acetyl-5-(4-aminophenyl)-8,9-dihydro-8-methyl-7H-1,3-dioxolo[4,5-h][2,3]benzodiazepine); ceftriaxone ((6R,7R)-7-[[(2Z)-2-(2-amino-1,3-thiazol-4-yl)-2-methoxyiminoacetyl]amino]-3-[(2-methyl-5,6-dioxo-1H-1,2,4-triazin-3-yl)sulfanylmethyl]-8-oxo-5-thia-1-azabicyclo [4.2.0]oct-2-ene-2-carboxylic acid); an inhibitor of glutamate carboxypeptidase II.

In one embodiment, the tyrosine kinase inhibitor of the invention, or a pharmaceutically acceptable salt or solvate thereof, is administered in combination with an antiglutamate compound.

In one embodiment, the tyrosine kinase inhibitor of the invention, or a pharmaceutically acceptable salt or solvate thereof, is administered in combination with riluzole.

In one embodiment, the tyrosine kinase inhibitor of the invention, or a pharmaceutically acceptable salt or solvate thereof, is an inhibitor of at least one tyrosine kinase selected from c-Kit, Lyn, Fyn, PDGFR and CSF1R, or any combination thereof, and is administered in combination with riluzole.

In one embodiment, the inhibitor of mast cell activity of the invention is administered in combination with riluzole. In one embodiment, the inhibitor of microglia cell activity of the invention is administered in combination with riluzole.

The invention also relates to a method for treating non-aggressive or moderately aggressive ALS in a subject, preferably in a human patient, comprising administering masitinib, or a pharmaceutically acceptable salt or solvate thereof, in combination with riluzole, to subjects or patients in need thereof.

In one embodiment, said method of the invention is for the treatment of patients having a progression of ALSFRS-R score before treatment initiation of less than 0.8 points per month. In another embodiment, said method of the invention is for the treatment of patients having a progression of ALSFRS-R score before treatment initiation of less than 1.1 points per month and equal to or greater than 0.8 points per month (≥0.8 to <1.1 points per month)

Riluzole may be administered at a dose of 50 to 200 mg/day, for example 50, 100, or 200 mg/day, preferably 50 mg twice daily.

In one embodiment, the tyrosine kinase inhibitor of the invention, or a pharmaceutically acceptable salt or solvate thereof, is administered in combination with topiramate.

In one embodiment, the tyrosine kinase inhibitor of the invention, or a pharmaceutically acceptable salt or solvate thereof, is administered in combination with gabapentin.

In one embodiment, the tyrosine kinase inhibitor of the invention, or a pharmaceutically acceptable salt or solvate thereof, is administered in combination with lamotrigine.

In one embodiment, the tyrosine kinase inhibitor of the invention, or a pharmaceutically acceptable salt or solvate thereof, is administered in combination with talampanel.

In one embodiment, the tyrosine kinase inhibitor of the invention, or a pharmaceutically acceptable salt or solvate thereof, is administered in combination with ceftriaxone.

In one embodiment, the tyrosine kinase inhibitor of the invention, or a pharmaceutically acceptable salt or solvate thereof, is administered in combination with an inhibitor of glutamate carboxypeptidase II.

In one embodiment, the tyrosine kinase inhibitor of the invention, or a pharmaceutically salt or solvate thereof, is administered simultaneously, separately or sequentially with at least one pharmaceutically active ingredient.

In one embodiment, the tyrosine kinase inhibitor of the invention, or a pharmaceutically salt or solvate thereof, is administered in combination with said at least one pharmaceutically active ingredient in a combined preparation for simultaneous, separate, or sequential use.

Regarding best dosage regimen, the tyrosine kinase inhibitor or a pharmaceutically acceptable salt or solvate thereof for use in the method of the invention, especially masitinib or a pharmaceutically acceptable salt or solvate thereof, is to be administered at a daily dose ranging from about 1.0 to about 9.0 mg/kg/day (mg per kilo body weight per day). In one embodiment, the tyrosine kinase inhibitor of the invention, or a pharmaceutically salt or solvate thereof, preferably masitinib or a pharmaceutically acceptable salt or solvate thereof, and more preferably masitinib mesilate, is administered at a daily dose of between about 1.5 to about 7.5 mg/kg/day; for example, about 1.5, about 3.0, about 4.5, about 6.0, or about 7.5 mg/kg/day, more preferably about 3.0, about 4.5 or about 6.0 mg/kg/day (mg per kg bodyweight per day).

Nonetheless said tyrosine kinase inhibitor or a pharmaceutically acceptable salt or solvate thereof, especially masitinib or a pharmaceutically acceptable salt or solvate thereof, can be dose escalated by increments of about 1.5 mg/kg/day in low responder patients to reach a maximum of about 7.5 mg/kg/day, more preferably about 4.5 or about 6.0 mg/kg/day. Each dose escalation is subjected to toxicity controls with an absence of any toxicity events permitting dose escalation to occur.

In one embodiment dose escalation of said tyrosine kinase inhibitor or a pharmaceutically acceptable salt or solvate thereof occurs at any time-point after at least 4 weeks after the initial dose has been administered and prior to 26 weeks after the initial dose has been administered; for example at week-4, week-8, week-12, week-16, week-20, or week-24. Each dose escalation is subjected to toxicity controls, including but not limited to: previous 4-week treatment period at a constant dose of study treatment and no suspected severe adverse event was reported and no suspected adverse event led to treatment interruption and no suspected adverse event is ongoing at the time of the dose increase, regardless of its severity. In the absence of any of the above-mentioned toxicity events, the predefined dose escalation may occur. In the case of an ongoing non-severe suspected adverse event at the time of the dose escalation or treatment interruption without dose reduction at time of treatment resumption, any dose increase is delayed until after an additional 4-week treatment period. No dose escalation will be authorized for patients who have had a dose reduction for safety reasons.

In one embodiment said tyrosine kinase inhibitor or a pharmaceutically acceptable salt or solvate thereof, preferably masitinib or a pharmaceutically acceptable salt or solvate thereof, is initially administered per os, preferably in two daily intakes, at a dose of 3 mg/kg/day during 6 weeks, then 4.5 mg/kg/day during 6 weeks, and then 4.5 mg/kg/day thereafter. In another embodiment, said tyrosine kinase inhibitor or a pharmaceutically acceptable salt or solvate thereof, preferably masitinib or a pharmaceutically acceptable salt or solvate thereof, is initially administered per os, preferably in two daily intakes, at a dose of 3.0 mg/kg/day during 12 weeks, and then 4.5 mg/kg/day thereafter.

In another example, masitinib or a pharmaceutically acceptable salt or solvate thereof is initially administered per os, preferably in two daily intakes, at a dose of 3 mg/kg/day during 4 weeks, then 4.5 mg/kg/day during 4 weeks, and then 6 mg/kg/day thereafter, with each dose escalation being subjected to toxicity controls.

In one embodiment, the tyrosine kinase inhibitor or a pharmaceutically acceptable salt or solvate thereof, preferably masitinib or a pharmaceutically acceptable salt or solvate thereof, and more preferably masitinib mesilate, is initially administered at a dose of 4.5 mg/kg/day during at least 6 weeks, then 6.0 mg/kg/day during at least 6 weeks, and at 6.0 mg/kg/day thereafter, with each dose escalation being subjected to toxicity controls.

Any dose indicated herein refers to the amount of active ingredient as such, not to its salt form.

Given that the masitinib dose in mg/kg/day used in the described dose regimens refers to the amount of active ingredient masitinib, compositional variations of a pharmaceutically acceptable salt of masitinib mesilate will not change the said dose regimens.

In a particular embodiment, masitinib or a pharmaceutically acceptable salt or solvate thereof may further be administered via different routes of administration but oral administration is preferred. In one embodiment, the tyrosine kinase inhibitor of the invention, or a pharmaceutically acceptable salt or solvate thereof, is administered orally. In one embodiment, the tyrosine kinase inhibitor of the invention, or a pharmaceutically acceptable salt or solvate thereof, is administered in two daily intakes. Thus, in still another preferred embodiment, in the use or the method above, masitinib or salts or solvates thereof, is administered orally; preferably twice a day for long term period such as over more than 6 months, preferably more than 12 months. Masitinib or a pharmaceutically acceptable salt or solvate thereof can be administered in the form of 100 and 200 mg tablets.

In one embodiment, the tyrosine kinase inhibitor or a pharmaceutically acceptable salt or solvate thereof, preferably masitinib or a pharmaceutically acceptable salt or solvate thereof, and more preferably masitinib mesilate, is comprised in a pharmaceutical composition in an amount of at least 50 mg and less than 600 mg, preferably of at least 100 mg and less than 400 mg.

The present invention also relates to a pharmaceutical composition comprising the tyrosine kinase inhibitor of the invention, or a pharmaceutically acceptable salt or solvate thereof.

The present invention also relates to a medicament comprising the tyrosine kinase inhibitor of the invention, or a pharmaceutically acceptable salt or solvate thereof.

The present invention also relates to a kit comprising the tyrosine kinase inhibitor of the invention, or a pharmaceutically acceptable salt or solvate thereof.

In one embodiment, the pharmaceutical composition, the medicament or the kit of the invention comprises masitinib or a pharmaceutically acceptable salt or solvate thereof.

In one embodiment, the pharmaceutical composition, the medicament or the kit of the invention comprises the tyrosine kinase inhibitor of the invention, or a pharmaceutically acceptable salt or solvate thereof, in combination with at least one other pharmaceutically active ingredient. In one embodiment, the pharmaceutical composition, the medicament or the kit of the invention comprises the tyrosine kinase inhibitor of the invention, or a pharmaceutically acceptable salt or solvate thereof, in combination with at least one other pharmaceutically active ingredient, preferably an antiglutamate compound, especially riluzole; topiramate; gabapentin; lamotrigine; talampanel; ceftriaxone; an inhibitor of Glutamate carboxypeptidase II, preferably said other pharmaceutically active ingredient is riluzole.

In one embodiment, the pharmaceutical composition, the medicament or the kit of the invention comprises the tyrosine kinase inhibitor of the invention, or a pharmaceutically acceptable salt or solvate thereof, in combination with at least one antiglutamate compound and/or an inhibitor of Glutamate carboxypeptidase II. In one embodiment, the pharmaceutical composition, the medicament or the kit of the invention comprises the tyrosine kinase inhibitor of the invention, or a pharmaceutically acceptable salt or solvate thereof, in combination with at least one other pharmaceutically active ingredient selected from the group comprising riluzole, topiramate, gabapentin, lamotrigine, talampanel, and ceftriaxone.

In one embodiment, the pharmaceutical composition, the medicament or the kit of the invention comprises the tyrosine kinase inhibitor of the invention, or a pharmaceutically acceptable salt or solvate thereof, in combination with riluzole. In a preferred embodiment, the medicament or the kit of the invention comprises masitinib, or a pharmaceutically acceptable salt or solvate thereof, in combination with riluzole.

According to a particular embodiment, the pharmaceutical composition or the medicament of the invention is thus an oral composition.

As is known to the person skilled in the art, various forms of excipients can be used adapted to the mode of administration and some of them can promote the effectiveness of the active molecule, e.g. by promoting a release profile rendering this active molecule overall more effective for the treatment desired.

Pharmaceutical compositions, medicaments or compositions for use in the method of the invention are thus able to be administered in various forms, more specially for example in an injectable, pulverizable or ingestible form, for example via the intramuscular, intravenous, subcutaneous, intradermal, oral, topical, rectal, vaginal, ophthalmic, nasal, transdermal or parenteral route. A preferred route is oral administration.

The present invention notably covers the use of a compound according to the present invention for the manufacture of a pharmaceutical composition or a medicament.

Such medicament or pharmaceutical composition can take the form of a medicament or pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

EXAMPLES

The present invention is further illustrated by the following examples.

Example 1

Study AB10015
Design:
Study AB10015 is a prospective, multicenter, randomized, double-blind, placebo-controlled, parallel groups, phase 2/3 study to compare the efficacy and safety of masitinib in combination with riluzole versus placebo in combination with riluzole in the treatment of patients suffering from amyotrophic lateral sclerosis (ALS).
Randomization:
381 patients were randomized in 3 groups:
Group 1: 127 patients received masitinib at 4.5 mg/kg/day+riluzole
Group 2: 127 patients received masitinib at 3 mg/kg/day+riluzole
Group 3: 127 patients received placebo+riluzole
Subgroup Analyses (Subpopulations of ALS Patients):
There are two distinct populations of ALS patients: a subpopulation of "normal progressors" and a subpopulation of "faster progressors". The targeted population for primary analysis is the subpopulation of "normal progressors".
Population of "normal progressors":
"Normal progressors" are defined as ALS patients whose progression of ALSFRS-R score before randomization is less than 1.1 point per month. This population should represent about 80% of ALS patients.
Population of "Normal Progressors+Faster Progressors":
The population of "normal progressors+faster progressors" comprises all ALS patients, "normal progressor" ALS patients or "faster progressor" ALS patients. "Faster progressors" are defined as ALS patients whose progression of ALSFRS-R score before randomization is greater than or equal to 1.1 points per month.
Main Inclusion Criteria:
Female or male patient aged between 18 and 75 years of age, with a weight >50 kg and body mass index between 18 and 35 kg/m$^2$;
Familial or sporadic ALS;

Patient diagnosed with laboratory supported, clinically probable or definite ALS according to the World Federation of Neurology Revised El Escorial criteria [Brooks B R. Journal of the Neurological Sciences 1994; 124(Suppl):96-107];

Disease duration from symptoms onset no longer than 36 months at the screening visit;

Patient treated with a stable dose of riluzole (100 mg/day) for at least 30 days prior to screening;

Patient with a FVC (Forced Vital Capacity) equal to or more than 60% predicted normal value for gender, height, and age at the screening visit;

Patient with adequate organ function at screening and baseline.

Main Exclusion Criteria:

Patient who underwent tracheotomy and/or gastrostomy.

Treatment Administration

Subjects enrolled received a total daily dose of 4.5 or 3 mg/kg masitinib, or a matching placebo, to be taken during meals as indicated in the Tables 2 and 3 below. For the morning dose, tablets were taken during breakfast. In case of nausea, the administration took place during lunch. For the evening dose, tablets were taken during dinner.

Study treatment daily dose of 4.5 mg/kg was administered in divided doses as indicated in Table 2

TABLE 2

Dose of study treatment (mg) to be administered according to patient's weight (4.5 mg/kg/day)

| Patient's weight in kg | | Daily dose (mg) | Morning (mg) | Evening (mg) |
|---|---|---|---|---|
| | ≤55.5 | 200 | 100 | 100 |
| >55.5 | ≤77.7 | 300 | 100 | 200 |
| >77.7 | ≤99.9 | 400 | 200 | 200 |
| >99.9 | | 500 | 200 | 200 + 100 |

4.5 mg/kg/day

Study treatment daily dose of 3 mg/kg was administered in divided doses as indicated in Table 3.

TABLE 3

Dose of study treatment (mg) to be administered according to patient's weight (3 mg/kg/day)

| Patient's weight in kg | | Daily dose (mg) | Morning (mg) | Evening (mg) |
|---|---|---|---|---|
| | ≤49.9 | NOT POSSIBLE | | |
| >49.9 | ≤83.3 | 200 | 100 | 100 |
| >83.3 | | 300 | 100 | 200 |

3 mg/kg/day

Analysis Datasets:

Intention-To-Treat (ITT) dataset—The ITT population is defined as all randomized patients, whether they have received the study treatment or not, with at least one post baseline efficacy assessment.

Modified Intent-To-Treat (mITT) dataset—The mITT population will include all ITT patients with probable or definite amyotrophic lateral sclerosis who took at least one dose of study treatment (masitinib or placebo).

Per Protocol (PP) dataset—The PP population consists of all patients of the mITT population without any major protocol deviation. This is the set of patients who participated in the study as intended. Patients terminating the study prematurely will be included in the PP population provided that there is no protocol deviation. Before locking the data base, the precise reasons for excluding patients from the PP population will be fully defined and documented by the Data Review Committee.

Safety population—The safety population (SAF) consists of all enrolled patients who took at least one dose of study medication (masitinib or placebo).

Statistical Methods

Primary endpoint:

Change from baseline to week 48 in the revised Amyotrophic Lateral Sclerosis Functional Rating Scale (ALSFRS-R)

Secondary endpoints:

Secondary analyses include the following endpoints:

Progression free survival (PFS), defined as ALSFRS-R deterioration of more than 9 points or death;

Combined Assessment of Function and Survival (CAFS);

Survival defined as the time from randomization to the date of documented death or first tracheotomy;

Time to first tracheotomy defined as the time from randomization to the time of the first tracheotomy;

Change of Forced Vital Capacity (FVC) from baseline to each time point (week 4, 8, 12, 24, 36, 48);

Change from baseline to each time point (week 4, 8, 12, 24 and 36) in ALSFRS-R;

Survival rate defined as the rate of patients alive without tracheotomy at each time point (week 12, 24, 36 and 48).

Interim Analysis

One interim analysis was planned for this study with around 50% of patients randomized.

The interim analysis was performed without any unblinding. An independent Contract Research Organization (CRO) was mandated to perform the analysis. The results were sent directly to the Independent Data Monitoring Committee (IDMC) members.

The IDMC concluded that study AB10015 met its primary objective based on the preplanned interim analysis. A small team of three people, without access to the patient randomization list and independent from the conduct of the study, was set-up and collected top-line data.

Example 2

Clinical data show that masitinib provides therapeutic benefit to a highly distinct subpopulation of ALS patients. These patients are identified as having non-aggressive or moderately aggressive ALS ("normal progressors"), defined as an ALS patient whose progression of ALSFRS-R score before treatment initiation was less than 1.1 points per month.

Study AB10015 Interim Analysis

Methods:

The study protocol and statistical analysis plan included provision to analyze two subgroups of patients: "normal progressors" (patients whose progression of ALSFRS-R score before randomization is less than 1.1 point per month, referred to also as patients with non-aggressive or moderately aggressive ALS) and "faster progressors" (patients whose progression of ALSFRS-R score before randomization is greater than or equal to 1.1 points per month, referred to also as patients with aggressive ALS).

In accordance with study AB10015 protocol, an interim analysis was planned to be performed after around 50% of the information became available for analysis. At the time of the interim analysis, 192 (50%) out of a planned 381 patients who had been randomized before the 12 Feb. 2015 could have reached the week 48 visit. This interim ITT population consisted of 65, 64 and 63 patients randomized to the placebo, masitinib 4.5 mg/kg/day, and masitinib 3.0 mg/kg/day cohorts, respectively. Among the 192 patients, 161 (85%) were "normal progressor" patients consisting of 54, 53 and 54 patients randomized to the placebo, masitinib 4.5 mg/kg/day, and masitinib 3.0 mg/kg/day cohorts, respectively. The randomization ratio according to dose (3 mg/kg/day vs. 4.5 mg/kg/day) was 1:1 (50%); consequently, the number of patients required for the interim analysis was achieved with respect to overall patient number, subpopulation status and treatment dose.

The interim analysis primary endpoint is based on the change from baseline to week 48 in ALSFRS-R. Primary analysis was performed in the mITT "normal progressor" (i.e. non-aggressive or moderately aggressive ALS) subpopulation. This analysis was done on patients randomized at an initial masitinib dose of 4.5 mg/kg/day (Group 1, n=52) versus placebo patients (Group 3, n=46) at a 3.11% alpha-level. Missing values of ALSFRS-R at study visit were replaced based on the Modified Last Observation Carried Forward (mLOCF) method.

Absolute change from baseline to week 48 in ALSFRS-R was estimated using a model of analysis of covariance (ANCOVA) adjusted on following factors: treatment (masitinib or placebo), and stratification criteria of: ALS patient subpopulation, progression of ALSFRS-R score (point/month) from date of first symptom to baseline, ALSFRS-R score at baseline, site of onset (bulbar versus others), age at baseline; and geographical region.

Two-sided (1-alpha) confidence interval of the difference of mean change from baseline to week 48 between groups was calculated. The primary analysis used a re-randomization test. The re-randomization test, also referred to as a randomization test or permutation test, is a type of statistical significance test in which the distribution of the test statistic under the null hypothesis is obtained by calculating all possible values of the test statistic under rearrangements of the labels on the observed data points. The proportion of replicates for which the p-value of treatment factor is at least as small as the p-value of treatment factor from the original data was calculated. In this proportion the observed p-value of treatment factor is also accounted for as one replicate in numerator and denominator. This proportion is the p-value for the randomization test. The hypothesis of no treatment difference was rejected at the 3.11% level of significance if the randomization p-value was lower or equal than 3.11%.

To control overall family-wise type I error rate at the study level, analyses of efficacy was conducted in a stepwise manner (fixed sequence method). Fixed sequence method ensures that the population claimed and treated with a selected dosage will be done by controlling the global family-wise error rate at the 0.0311 level for the primary analysis. Sequence 1 was performed on the 4.5 mg/kg/day randomized "normal progressor" patient cohort. Primary analysis was absolute change (calculated via the 'least squares means' methodology) from baseline to week 48 in ALSFRS-R score. Analysis was considered conclusive at a 0.0311 significance level.

Results:
In general, patient demographics and baseline characteristics were well-matched between treatment-arms and subpopulations. For analysis of masitinib's treatment effect according to progression of ALSFRS-R score in the distinct subgroups of non-aggressive or moderately aggressive ALS (i.e. normal progressors) versus aggressive ALS (i.e. faster progressors) a comparison was made between the following cohorts.

i) Change in ALSFRS-R (primary endpoint) from baseline to week 48 in the 4.5 mg/kg/day randomized "normal progressor" patient cohort, according to treatment-arm (masitinib versus placebo). This corresponds to the interim analysis primary analysis, i.e. sequence 1 of the stepwise fixed sequence method.

A total of 98 patients were assessable for the first sequence of the interim analysis primary endpoint, i.e. patients from the "normal progressor" subgroup with assessable baseline and week-48 data, randomized to either the masitinib 4.5 mg/kg/day treatment-arm (n=46) or the placebo arm (n=52). Mean exposure to masitinib (4.5 mg/kg/day) or placebo in this cohort was 9.5±2.8 months (range 1.7-11.5 months) and 9.3±3.2 months (0.2-13.3 months), respectively.

Masitinib showed a significant improvement over placebo in its primary endpoint, with an average decrease in ALSFRS-R score of 14.51 points for placebo treated patients compared with a decrease of 9.02 for masitinib treated patients, P=0.0032 (Table 4). Masitinib administered at 4.5 mg/kg/day therefore generated a statistically significant retardation of disease progression as measured by ALSFRS-R score in the ALS 'normal progressors' subpopulation.

TABLE 4

Primary analysis for the "normal progressor" subpopulation (progression of ALSFRS-R score < 1.1 points/month) comparing patients randomized to the masitinib 4.5 mg/kg/day arm with the placebo arm (interim AB10015)

| Normal progressor subgroup | N[†] | Δ ALSFRS-R | Delta [CI][‡] | p-value* |
|---|---|---|---|---|
| Placebo | 46 | −14.51 | 5.49 [1.31; 9.66] | 0.0032 |
| Masitinib (4.5) | 52 | −9.02 | | |

[†]Patients assessable for primary efficacy analysis.
*P-value is based on re-randomization. Interim analysis level of significance set at <0.0311.
Δ ALSFRS-R = (least squares means) change from baseline to week 48 in ALSFRS-R score.
Masitinib (4.5) = randomization Group 1 receiving masitinib at 4.5 mg/kg/day plus riluzole.
[‡]Delta = absolute difference (masitinib − placebo) between treatment-arms.
[CI] = (1-alpha) confidence interval, mITT population.

ii) Change in ALSFRS-R from baseline to week 48 in the 4.5 mg/kg/day randomized patient cohort directly comparing treatment effect between the subpopulations of masitinib-treated 'normal progressors' versus masitinib-treated 'faster progressors'.

Masitinib treatment of normal progressor (non-aggressive or moderately aggressive ALS) patients showed a strong statistically significant improvement over faster progressor (aggressive ALS) patients in terms of ALSFRS-R score, with an average decrease in ALSFRS-R score of 5.57 points versus a decrease of 17.9 points, respectively, P=0.0004 (Table 5). Masitinib administered at 4.5 mg/kg/day therefore generated an unexpectedly strong retardation of disease progression as measured by ALSFRS-R score in the ALS 'normal progressor' subpopulation when compared to with the ALS 'faster progressor' subpopulation.

Unexpectedly, these data show that the positive treatment effect demonstrated for masitinib versus placebo in the primary analysis is therefore strongly driven by the 'normal progressor' subpopulation. Masitinib is therefore highly effective in this subpopulation of non-aggressive or moderately aggressive ALS patients (normal progressors) and less effective or of limited effectiveness in aggressive ALS patients (faster progressors).

TABLE 5

Analysis for masitinib (4.5 mg/kg/day) treated patients comparing subpopulations of 'normal progressors' (progression of ALSFRS-R score < 1.1 points/month) versus 'faster progressors' (progression of ALSFRS-R score ≥ 1.1 points/month) (interim AB10015)

| Masitinib treatment effect | N[†] | Δ ALSFRS-R | Delta [CI][‡] | P-value |
|---|---|---|---|---|
| Normal progressors | 52 | −5.57 | −12.33 [−19.52; −5.14] | 0.0004 |
| Faster progressors | 10 | −17.90 | | |

[†]Patients assessable for primary efficacy analysis. Interim analysis level of significance set at <0.0311.
Δ ALSFRS-R = (least squares means) change from baseline to week 48 in ALSFRS-R score.
[‡]Delta = absolute difference (normal progressor − faster progressor) between treatment-arms.
[CI] = (1-alpha) confidence interval, mITT population.

iii) Change in ALSFRS-R from baseline to week 48 in the 4.5 mg/kg/day randomized "faster progressor" patient cohort, according to treatment-arm (masitinib versus placebo).

The observation that masitinib is of limited effectiveness in aggressive ALS patients (see Table 5 above) is confirmed by analysis of ALSFRS-R change from baseline to week 48 in the 4.5 mg/kg/day randomized "faster progressor" patient cohort, according to treatment-arm (masitinib versus placebo).

No significant difference was seen between treatment-arms in the 'faster progressor' subpopulation. Indeed, there was no trend towards retardation of disease progression in this patient subpopulation (masitinib treated patients showed a greater average decrease in ALSFRS-R score when compared with placebo treated patients) (Table 6). This observation supports the unexpected result that masitinib is only effective in non-aggressive or moderately aggressive ALS patients (normal progressors), supporting the hypothesis that different mechanisms of disease progression are in part responsible for survival heterogeneity within the overall ALS population.

TABLE 6

Analysis for the "faster progressor" subpopulation (progression of ALSFRS-R score ≥ 1.1 points/month) comparing patients randomized to the masitinib 4.5 mg/kg/day arm with the placebo arm (interim analysis AB10015)

| Faster progressor subgroup | N[†] | Δ ALSFRS-R | Delta [CI][‡] | P-value |
|---|---|---|---|---|
| Placebo | 11 | −16.31 | −4.46 [−17.63; 8.71] | 0.4327 |
| Masitinib (4.5) | 10 | −20.77 | | |

[†]Patients assessable for primary efficacy analysis. Interim analysis level of significance set at <0.0311.
Δ ALSFRS-R = (least squares means) change from baseline to week 48 in ALSFRS-R score.
Masitinib (4.5) = randomization Group 1 receiving masitinib at 4.5 mg/kg/day plus riluzole.
[‡]Delta = absolute difference (masitinib − placebo) between treatment-arms.
[CI] = (1-alpha) confidence interval. mITT population.

Taken together, these data demonstrate that masitinib generates a clinical advantage in the restricted population of non-aggressive or moderately aggressive ALS (i.e. patients whose progression of ALSFRS-R score before randomization is less than 1.1 point per month) that is unexpectedly superior to the other patient cohort suffering from aggressive ALS (i.e. patients whose progression of ALSFRS-R score before randomization is ≥1.1 point per month). These findings support the use of progression of ALSFRS-R score before treatment initiation with a threshold of less than 1.1 points per month as an independent predictor factor for masitinib treatment efficacy and patient selection from among the overall ALS population.

Example 3

Final analysis of study AB10015 was performed when 100% of the information became available. Clinical data from this final analysis confirmed findings from the AB10015 interim analysis, showing that masitinib provides therapeutic benefit to a highly distinct subpopulation of ALS patients. These patients are identified as being normal progressors, defined as ALS patients whose progression of ALSFRS-R score before treatment initiation was less than 1.1 points per month (comprising non-aggressive and moderately aggressive ALS patients as defined hereinabove).

Study AB10015 Final Analysis

Database cutoff was on 16 Mar. 2017. The data presented in this example are in part taken from preliminary analysis and as such represent a close approximation to the final, validated dataset.

To determine the effect of the administration of masitinib according to progression of ALSFRS-R score in distinct subpopulations of the overall ALS patient population, the following analyses were conducted.

i) Change in ALSFRS-R (primary endpoint) from baseline to week 48 in the 4.5 mg/kg/day randomized patient cohort, according to treatment-arm (masitinib versus placebo). This corresponds to the final analysis primary endpoint.

Masitinib administered at 4.5 mg/kg/day generated a statistically significant retardation of disease progression as measured by ALSFRS-R score in the ALS 'normal progressors' subpopulation (<1.1 points per month). Masitinib showed a significant improvement over placebo in its primary endpoint (P=0.0142), with an average decrease in ALSFRS-R score of −8.7 points versus −12.1 points between masitinib and placebo, respectively (corresponding to a difference of 3.4 points) (Table 7).

TABLE 7

Primary analysis for the "normal progressor" subpopulation (progression of ALSFRS-R score of less than 1.1 points per month) comparing patients randomized to the masitinib 4.5 mg/kg/day arm with the placebo arm (final AB10015)

| Normal progressor subgroup (<1.1 pts/m) | N[†] | Δ ALSFRS-R | Delta [CI][‡] | P-value |
|---|---|---|---|---|
| Placebo | 102 | −12.1005 | 3.396[0.69; 6.102] | 0.0142 |
| Masitinib (4.5) | 99 | −8.7045 | | |

[†]Patients assessable for primary efficacy analysis. Final analysis level of significance set at <0.05.
Δ ALSFRS-R = (least squares means) change from baseline to week 48 in ALSFRS-R score.
Masitinib (4.5) = randomization Group 1 receiving masitinib at 4.5 mg/kg/day plus riluzole.
[‡]Delta = absolute difference (masitinib − placebo) between treatment-arms.
[CI] = (1-alpha) confidence interval. mITT population.

Considering the subgroup of 'non-aggressive ALS' patients (<0.8 points per month), masitinib generated a retardation in ALSFRS-R score corresponding to a difference of 3.4 points (−8.3 points versus −11.7 points for masitinib and placebo, respectively). (Table 8).

TABLE 8

Primary analysis for the "non-aggressive" ALS subgroup (progression of ALSFRS-R score of less than 0.8 points per month) comparing patients randomized to the masitinib 4.5 mg/kg/day arm with the placebo arm (final AB 10015)

| Non-aggressive subgroup (<0.8 pts/m) | N† | Δ ALSFRS-R | Delta [CI]‡ | P-value |
|---|---|---|---|---|
| Placebo | 90 | −11.7479 | 3.4927[0.6689; 6.3165] | 0.0156 |
| Masitinib (4.5) | 85 | −8.2552 | | |

†Patients assessable for efficacy analysis. Final analysis level of significance set at <0.05.
Δ ALSFRS-R = (least squares means) change from baseline to week 48 in ALSFRS-R score.
Masitinib (4.5) = randomization Group 1 receiving masitinib at 4.5 mg/kg/day plus riluzole.
‡Delta = absolute difference (masitinib − placebo) between treatment-arms.
[CI] = (1-alpha) confidence interval. mITT population.

Considering the subgroup of 'moderately aggressive ALS' patients (≥0.8 to <1.1 points per month), masitinib generated a retardation in ALSFRS-R score corresponding to a difference of 2.2 points (−11 points versus −13.2 points for masitinib and placebo, respectively) (Table 9). It is noted that the cohort of patients with moderately aggressive ALS (progression of ALSFRS-R score of ≥0.8 to <1.1 points per month) is smaller than the cohort of patients with non-aggressive ALS (progression of ALSFRS-R score <0.8 points per month).

TABLE 9

Primary analysis for the "moderately aggressive" ALS subgroup (progression of ALSFRS-R score of ≥0.8 to <1.1 points per month) comparing patients randomized to the masitinib 4.5 mg/kg/day arm with the placebo arm

| Moderately aggressive subgroup (≥0.8 to <1.1 pts/m) | N† | Δ ALSFRS-R | Delta [CI]‡ | P-value |
|---|---|---|---|---|
| Placebo | 12 | −13.2317 | 2.2286[−8.5934; 13.0505] | 0.6704 |
| Masitinib (4.5) | 14 | −11.0031 | | |

†Patients assessable for efficacy analysis. Final analysis level of significance set at <0.05.
Δ ALSFRS-R = (least squares means) change from baseline to week 48 in ALSFRS-R score.
Masitinib (4.5) = randomization Group 1 receiving masitinib at 4.5 mg/kg/day plus riluzole.
‡Delta = absolute difference (masitinib − placebo) between treatment-arms.
[CI] = (1-alpha) confidence interval. mITT population.

No significant difference was seen between treatment-arms in the 'faster progressors' subpopulation (≥1.1 points per month) confirming that masitinib (4.5 mg/kg/day) is of limited effectiveness in faster progressor ALS patients and not applicable to the overall ALS population (see Table 10). Indeed, there was no trend towards retardation of disease progression in this patient subpopulation. This observation supports the unexpected result that masitinib is only effective in normal progressor ALS patients (comprising non-aggressive ALS and moderately aggressive ALS subpopulations as defined hereinabove).

TABLE 10

Primary analysis for the "faster progressor" subpopulation (progression of ALSFRS-R score of ≥ 1.1 points per month) comparing patients randomized to the masitinib 4.5 mg/kg/day arm with the placebo arm (final AB10015)

| Faster progressor subgroup (≥1.1 pts/m) | N† | Δ ALSFRS-R | Delta [CI]‡ | P-value |
|---|---|---|---|---|
| Placebo | 17 | −14.1783 | −3.7485[−12.8419; 5.345] | 0.4069 |
| Masitinib (4.5) | 21 | −17.9268 | | |

†Patients assessable for primary efficacy analysis. Final analysis level of significance set at <0.05.
Δ ALSFRS-R = (least squares means) change from baseline to week 48 in ALSFRS-R score.
Masitinib (4.5) = randomization Group 1 receiving masitinib at 4.5 mg/kg/day plus riluzole.
‡Delta = absolute difference (masitinib − placebo) between treatment-arms.
[CI] = (1-alpha) confidence interval. mITT population.

Importantly, it was shown that no significant difference (P=0.11) was seen between treatment-arms in the overall study population (i.e. a cohort comprising normal progressor and faster progressor patients, irrespective of progression of ALSFRS-R score before treatment initiation) (Table 11). Therefore, any study design based on treatment of the overall ALS population would have resulted in failure to demonstrate treatment effect. This observation supports the unexpected result that masitinib is only effective in a restricted subpopulation of ALS patients and that identification of responsive patients represents new knowledge and could not have been predicted by teachings from the prior art.

TABLE 11

Primary analysis comparing patients randomized to the masitinib 4.5 mg/kg/day arm with the placebo arm for the overall study population "normal progressor and faster progressor" (irrespective of progression of ALSFRS-R score) (final AB10015)

| Overall study population | N† | Δ ALSFRS-R | Delta [CI]‡ | P-value |
|---|---|---|---|---|
| Placebo | 119 | −12.8216 | 2.1197[−0.4994; 4.7388] | 0.1122 |
| Masitinib (4.5) | 120 | −10.7019 | | |

†Patients assessable for primary efficacy analysis. Final analysis level of significance set at <0.05.
Δ ALSFRS-R = (least squares means) change from baseline to week 48 in ALSFRS-R score.
Masitinib (4.5) = randomization Group 1 receiving masitinib at 4.5 mg/kg/day plus riluzole.
‡Delta = absolute difference (masitinib − placebo) between treatment-arms.
[CI] = (1-alpha) confidence interval. mITT population.

ii) Change in ALSFRS-R from baseline to week 48 in the 4.5 mg/kg/day randomized patient cohort directly comparing masitinib treatment effect between ALS subpopulations.

Masitinib treatment of normal progressor ALS patients showed a strong statistically significant treatment effect over faster progressor (aggressive ALS) patients in terms of ALSFRS-R score (P<0.001), with an average decrease in ALSFRS-R score of 8.4 points versus 19.6 points between normal progressors and faster progressors, respectively, (corresponding to a difference of 11.2 points) (Table 12). Masitinib administered at 4.5 mg/kg/day therefore generated an unexpectedly strong retardation of disease progression as measured by ALSFRS-R score in the ALS 'normal progressor' subpopulation when compared to the ALS 'faster progressor' subpopulation. Masitinib is therefore highly effective in the 'normal progressor' subpopulation (comprising non-aggressive ALS and moderately aggressive ALS subpopulations as defined hereinabove) and ineffective or of limited effectiveness in faster progressor ALS patients.

TABLE 12

Analysis for masitinib (4.5 mg/kg/day) treated patients comparing
subpopulations of 'normal progressors' versus 'faster progressors'

| Masitinib treatment effect | N[†] | Δ ALSFRS-R | Delta [CI][‡] | P-value |
|---|---|---|---|---|
| Normal progressors (<1.1 pts/m) | 99 | −8.3939 | −11.1916[−16.0776; −6.3056] | <.0001 |
| Faster progressors (>1.1 pts/m) | 21 | −19.5855 | | |

[†]Patients assessable for primary efficacy analysis. Final analysis level of significance set at <0.05.
Δ ALSFRS-R = (least squares means) change from baseline to week 48 in ALSFRS-R score.
[‡]Delta = absolute difference (normal progressor − faster progressor) between treatment-arms.
[CI] = (1-alpha) confidence interval. mITT population.

Similar statistically significant findings are shown for comparison of non-aggressive ALS patients (<0.8 points per month) versus aggressive ALS patients (≥1.1 points per month) (see table 13), and non-aggressive ALS patients (<0.8 points per month) versus moderately aggressive and aggressive ALS patients (≥0.8 points per month) (see table 14).

TABLE 13

Analysis for masitinib (4.5 mg/kg/day) treated patients comparing
subpopulations of 'non-aggressive' versus 'faster progressors (aggressive)'
(final AB10015)

| Masitinib treatment effect | N[†] | Δ ALSFRS-R | Delta [CI][‡] | P-value |
|---|---|---|---|---|
| Non-aggressive (<0.8 pts/m) | 85 | −7.4509 | −10.8411[−15.739; −5.9432] | <.0001 |
| Faster progressors (≥1.1 pts/m) | 21 | −18.2920 | | |

[†]Patients assessable for primary efficacy analysis. Final analysis level of significance set at <0.05.
Δ ALSFRS-R = (least squares means) change from baseline to week 48 in ALSFRS-R score.
[‡]Delta = absolute difference (normal progressor − faster progressor) between treatment-arms.
[CI] = (1-alpha) confidence interval. mITT population.

TABLE 14

Analysis for masitinib (4.5 mg/kg/day) treated patients comparing
subpopulations of 'non-aggressive' versus 'moderately aggressive
plus aggressive' (final AB10015)

| Masitinib treatment effect | N[†] | Δ ALSFRS-R | Delta [CI][‡] | P-value |
|---|---|---|---|---|
| Non-aggressive (<0.8 pts/m) | 85 | −7.8085 | −8.0995[−12.3719; −3.8271] | 0.0003 |
| Moderately aggressive plus aggressive (≥0.8 pts/m) | 35 | −15.9080 | | |

[†]Patients assessable for primary efficacy analysis. Final analysis level of significance set at <0.05.
Δ ALSFRS-R = (least squares means) change from baseline to week 48 in ALSFRS-R score.
[‡]Delta = absolute difference (normal progressor − faster progressor) between treatment-arms.
[CI] = (1-alpha) confidence interval. mITT population.

Masitinib treatment of moderately aggressive ALS patients (≥0.8 to <1.1 points per month) showed a strong trend in treatment effect over aggressive ALS patients (≥1.1 points per month) in terms of ALSFRS-R score, (see table 15).

TABLE 15

Analysis for masitinib (4.5 mg/kg/day) treated patients comparing
subpopulations of 'moderately aggressive' versus 'faster progressors
(aggressive)' (final AB10015)

| Masitinib treatment effect | N[†] | Δ ALSFRS-R | Delta [CI][‡] | P-value |
|---|---|---|---|---|
| Moderately aggressive (≥0.8 to <1.1 pts/m) | 14 | −15.7258 | −9.3308[−19.4226; 0.761] | 0.0687 |
| Faster progressors (≥1.1 pts/m) | 21 | −25.0567 | | |

[†]Patients assessable for primary efficacy analysis. Final analysis level of significance set at <0.05.
Δ ALSFRS-R = (least squares means) change from baseline to week 48 in ALSFRS-R score.
[‡]Delta = absolute difference (normal progressor − faster progressor) between treatment-arms.
[CI] = (1-alpha) confidence interval. mITT population.

In conclusion, these final analysis data from study AB10015 prove the following:

Masitinib is an effective treatment for ALS patients having progression of ALSFRS-R score prior to treatment initiation of less than 1.1 points per month (this subpopulation being collectively referred to as non-aggressive or moderately aggressive ALS).

Masitinib is most effective in treating patients having progression of ALSFRS-R score prior to treatment initiation of less than 0.8 points per month (this subpopulation being collectively referred to as non-aggressive ALS).

Masitinib is effective in treating patients having progression of ALSFRS-R score prior to treatment initiation of ≥0.8 to <1.1 points per month (this subpopulation being collectively referred to as moderately aggressive ALS), albeit to a lesser extent than for the non-aggressive subpopulation.

Masitinib is an ineffective treatment for ALS patients having progression of ALSFRS-R score prior to treatment initiation of at least 1.1 points per month (this subpopulation being collectively referred to as aggressive ALS).

The invention claimed is:

1. A method for treating amyotrophic lateral sclerosis (ALS) in a patient having a score progression, before treatment initiation, of less than 1.1 points per month according to the revised Amyotrophic Lateral Sclerosis Functional Rating Scale (ALSFRS-R), said method comprising administering to the patient an inhibitor of at least one tyrosine kinase selected from the group consisting of c-Kit, Lyn, Fyn, PDGFR, and CSF1R, and any combination thereof.

2. The method according to claim 1, wherein said patient has a score progression, before treatment initiation, of less than 0.8 points per month according to the ALSFRS-R.

3. The method according to claim 1, wherein said patient has a score progression, before treatment initiation, of less than 1.1 points per month and equal to or greater than 0.8 points per month (≥0.8 to <1.1 points per month) according to the ALSFRS-R.

4. The method according to claim 1, wherein said inhibitor is an inhibitor of mast cell activity.

5. The method according to claim 4, wherein said mast cell inhibitor is chosen from the group consisting of: masitinib, imatinib, cromolyn sodium, midostaurin, BLU-285, bosutinib, ibrutinib, LAS189386, DP-2618, fostamatinib, nilotinib, dasatinib, sunitinib, axitinib, pazopanib, and toceranib.

6. The method according to claim 1, wherein said inhibitor is an inhibitor of microglia cell activity.

7. The method according to claim 6, wherein said microglia cell inhibitor is chosen from the group consisting of: masitinib, GW2580, pexidartinib, BLZ945, linifanib, OSI-930, imatinib, sunitinib, nilotinib, pazopanib, emactuzumab, FPA008, quizartinib, axitinib, motesanib, cediranib, JNJ-28312141, Ki-20227, MLN-518, sorafenib, and SU-14813.

8. The method according to claim 1, wherein said inhibitor is a 2-aminoarylthiazole derivative.

9. The method according to claim 8, wherein said inhibitor is masitinib or a pharmaceutically acceptable salt or solvate thereof.

10. The method according to claim 9, wherein the pharmaceutically acceptable salt of masitinib is masitinib mesilate.

11. The method according to claim 1, wherein said inhibitor is administered at a dose ranging from about 1.0 to about 9.0 mg/kg/day (mg per kilo body weight per day).

12. The method according to claim 1, wherein said inhibitor is administered at an initial dose of 3.0 mg/kg/day during at least 4 weeks, then 4.5 mg/kg/day during at least 4 weeks, and at 6.0 mg/kg/day thereafter, with each dose escalation being subjected to toxicity controls.

13. The method according to claim 1, wherein said inhibitor is administered at a dose of 4.5 mg/kg/day.

14. The method according to claim 1, wherein said inhibitor is administered at a dose of 6 mg/kg/day.

15. The method according to claim 1, wherein said inhibitor is administered in two daily intakes.

16. The method according to claim 1, wherein said inhibitor is administered orally.

17. The method according to claim 1, wherein said inhibitor is administered in combination with at least one other pharmaceutically active ingredient.

18. The method according to claim 17, wherein said at least one other pharmaceutically active ingredient is an antiglutamate compound, or an inhibitor of glutamate carboxypeptidase II.

19. The method according to claim 18, wherein said antiglutamate compound is selected from the group consisting of riluzole, topiramate, gabapentin, lamotrigine, talampanel, and ceftriaxone.

20. The method according to claim 18, wherein said antiglutamate compound is riluzole.

* * * * *